(12) United States Patent
Magee et al.

(10) Patent No.: US 9,259,367 B2
(45) Date of Patent: Feb. 16, 2016

(54) DISPOSABLE ABSORBENT ARTICLE DESIGNED TO FACILITATE AN EASY CHANGE

(71) Applicant: The Procter & Gamble Company, Cincinnati, OH (US)

(72) Inventors: Luke Robinson Magee, Cincinnati, OH (US); George Bartol Glackin, III, Wyoming, OH (US); Christopher John Hosmer, Brighton, MA (US); Naomi Shoshana Korn, Chicago, IL (US); James Douglas Wilson, Norwood, MA (US); Mark Christopher Bates, Westwood, MA (US); Mattias Schmidt, Idstein (DE); Eva Susanne Dominique Thurnay, Frankfurt am Main (DE); Joerg Mueller, Karben (DE)

(73) Assignee: The Procter & Gamble, Cincinnati, OH (US)

( * ) Notice: Subject to any disclaimer, the term of this patent is extended or adjusted under 35 U.S.C. 154(b) by 191 days.

(21) Appl. No.: 13/942,975

(22) Filed: Jul. 16, 2013

(65) Prior Publication Data

US 2013/0304015 A1 Nov. 14, 2013

Related U.S. Application Data

(63) Continuation of application No. 12/824,425, filed on Jun. 28, 2010, now Pat. No. 8,492,608, and a (Continued)

(51) Int. Cl.
*A61F 13/15* (2006.01)
*A61F 13/84* (2006.01)
(Continued)

(52) U.S. Cl.
CPC .............. *A61F 13/84* (2013.01); *A61F 13/495* (2013.01); *A61F 13/51394* (2013.01);
(Continued)

(58) Field of Classification Search
CPC .................... A61F 13/51394; A61F 13/51496; A61F 2013/51377; A61F 2013/8497
USPC ........................................................ 604/361
See application file for complete search history.

(56) References Cited

U.S. PATENT DOCUMENTS 2,881,761 A 4/1959 Kenner
3,638,651 A 2/1972 Torr
(Continued)

FOREIGN PATENT DOCUMENTS

EP 0 605 730 A1 7/1994
EP 0 774 946 B1 5/1997
(Continued)

OTHER PUBLICATIONS

"Carefree Teens colored pantyliners, Personal Products, U.S.A., about 1990," Carefree Teens pantyliners for teenagers at the Museum of Menstruation and Women's Health (http://mum.org/crfrteen.htm), 3 pages.

(Continued)

*Primary Examiner* — Lynne Anderson
(74) *Attorney, Agent, or Firm* — Andrew J. Hagerty; George H. Leal

(57) ABSTRACT

A disposable absorbent article to be worn about the lower torso of a wearer that facilitates an easy, intuitive change is provided. The disposable absorbent article includes at least one serviceable indicium that facilitates an easy change by providing alignment of the article relative to an anatomical feature of the wearer or by externally highlighting one or more components of the article thereby indicating alignment and fit about the wearer's lower torso.

18 Claims, 21 Drawing Sheets

Related U.S. Application Data continuation of application No. 11/545,187, filed on Oct. 10, 2006, now Pat. No. 7,863,497, and a continuation of application No. 11/008,731, filed on Dec. 9, 2004, now Pat. No. 7,833,212, and a continuation of application No. 10/079,184, filed on Feb. 20, 2002, now abandoned.

(51) Int. Cl.
| | |
|---|---|
| *A61F 13/513* | (2006.01) |
| *A61F 13/495* | (2006.01) |
| *A61F 13/56* | (2006.01) |
| *G06Q 30/02* | (2012.01) |
| *G06Q 30/06* | (2012.01) |
| *G06Q 40/02* | (2012.01) |
| *A61F 13/514* | (2006.01) |

(52) U.S. Cl.
CPC ........... *A61F 13/5622* (2013.01); *G06Q 30/02* (2013.01); *G06Q 30/06* (2013.01); *G06Q 40/02* (2013.01); *A61F 13/51496* (2013.01); *A61F 2013/51377* (2013.01); *A61F 2013/8497* (2013.01)

(56) References Cited

U.S. PATENT DOCUMENTS

| | | | |
|---|---|---|---|
| 3,646,937 A | 3/1972 | Gellert | |
| 3,806,003 A | 4/1974 | Fujimoto | |
| 3,856,008 A | 12/1974 | Fowler et al. | |
| 3,869,761 A | 3/1975 | Schaar | |
| 4,014,340 A | 3/1977 | Cheslow | |
| 4,036,233 A | 7/1977 | Kozak | |
| 4,107,364 A | 8/1978 | Sisson | |
| 4,351,340 A | 9/1982 | Mcleod | |
| 4,381,781 A | 5/1983 | Sciaraffa et al. | |
| 4,397,646 A | 8/1983 | Daniels et al. | |
| 4,581,772 A | 4/1986 | Smith | |
| 4,615,695 A | 10/1986 | Cooper | |
| 4,623,340 A | 11/1986 | Luceri | |
| 4,662,875 A | 5/1987 | Hirotsu et al. | |
| 4,673,403 A | 6/1987 | Lassen et al. | |
| 4,834,741 A | 5/1989 | Sabee | |
| 4,857,067 A | 8/1989 | Wood et al. | |
| 4,892,536 A | 1/1990 | Desmarais et al. | |
| 4,908,026 A | 3/1990 | Sukiennik | |
| 4,909,879 A | 3/1990 | Ball | |
| 4,923,456 A | 5/1990 | Proxmire | |
| 4,936,840 A | 6/1990 | Proxmire | |
| 4,938,753 A | 7/1990 | Van Gompel et al. | |
| 4,990,147 A | 2/1991 | Freeland | |
| 5,006,394 A | 4/1991 | Baird | |
| 5,019,070 A | 5/1991 | Ruben | |
| 5,037,416 A | 8/1991 | Allen et al. | |
| 5,133,707 A | 7/1992 | Rogers et al. | |
| 5,151,092 A | 9/1992 | Buell et al. | |
| 5,167,897 A | 12/1992 | Weber et al. | |
| 5,188,625 A | 2/1993 | Vaniten | |
| 5,221,274 A | 6/1993 | Buell et al. | |
| 5,261,899 A | 11/1993 | Visscher | |
| 5,269,775 A | 12/1993 | Freeland et al. | |
| 5,275,588 A | 1/1994 | Matsumoto et al. | |
| 5,300,053 A | 4/1994 | Genaro | |
| 5,312,386 A | 5/1994 | Correa et al. | |
| 5,324,279 A | 6/1994 | Lancaster et al. | |
| 5,342,344 A | 8/1994 | Lancaster et al. | |
| H1376 H * | 11/1994 | Osborn et al. ................ 604/361 | |
| 5,401,267 A | 3/1995 | Couture-Dorschner | |
| 5,437,653 A | 8/1995 | Gilman | |
| 5,454,800 A | 10/1995 | Hirt | |
| 5,458,590 A | 10/1995 | Schleinz | |
| 5,477,507 A | 12/1995 | Kaplan | |
| 5,503,076 A | 4/1996 | Yeo | |
| 5,518,801 A | 5/1996 | Chappell et al. | |
| 5,531,731 A | 7/1996 | Brusky | |
| 5,554,145 A | 9/1996 | Roe et al. | |
| 5,558,659 A | 9/1996 | Sherrod et al. | |
| 5,558,734 A | 9/1996 | Sherrod et al. | |
| 5,562,037 A | 10/1996 | Schleinz | |
| 5,566,616 A | 10/1996 | Schleinz | |
| 5,569,234 A | 10/1996 | Buell et al. | |
| 5,580,411 A | 12/1996 | Nease et al. | |
| 5,624,422 A | 4/1997 | Allen | |
| 5,629,775 A | 5/1997 | Platteter et al. | |
| 5,650,214 A | 7/1997 | Anderson et al. | |
| 5,669,897 A | 9/1997 | Lavon et al. | |
| 5,675,079 A | 10/1997 | Gilman et al. | |
| 5,683,752 A | 11/1997 | Popp | |
| 5,702,382 A | 12/1997 | Osborn, III et al. | |
| 5,766,389 A | 6/1998 | Brandon et al. | |
| 5,772,649 A | 6/1998 | Siudzinski | |
| 5,779,690 A | 7/1998 | Gustafsson et al. | |
| 5,817,079 A | 10/1998 | Bergquist et al. | |
| 5,818,719 A | 10/1998 | Brandon | |
| 5,897,541 A | 4/1999 | Uitenbroek | |
| 5,897,546 A | 4/1999 | Kido et al. | |
| 5,904,673 A | 5/1999 | Roe et al. | |
| 5,906,008 A | 5/1999 | Heki et al. | |
| 6,004,306 A | 12/1999 | Robles et al. | |
| 6,045,543 A | 4/2000 | Pozniak et al. | |
| 6,075,178 A | 6/2000 | La Wilhelm | |
| 6,140,551 A | 10/2000 | Niemeyer et al. | |
| 6,251,097 B1 | 6/2001 | Kline et al. | |
| 6,264,640 B1 | 7/2001 | Sutton | |
| 6,297,424 B1 * | 10/2001 | Olson et al. ................ 604/361 | |
| 6,307,119 B1 | 10/2001 | Cammarota et al. | |
| 6,352,528 B1 * | 3/2002 | Weber et al. ............. 604/385.03 | |
| 6,444,064 B1 * | 9/2002 | Henry et al. .................... 156/64 | |
| 6,515,194 B2 * | 2/2003 | Neading et al. ................ 604/361 | |
| 6,545,197 B1 | 4/2003 | Muller et al. | |
| 6,595,042 B2 | 7/2003 | Holliday et al. | |
| 6,596,918 B1 | 7/2003 | Wehrle et al. | |
| 6,667,085 B1 | 12/2003 | Mcnichols | |
| 6,733,483 B2 | 5/2004 | Raufman et al. | |
| 6,888,044 B2 | 5/2005 | Fell et al. | |
| 6,946,585 B2 | 9/2005 | London Brown | |
| 7,163,528 B2 | 1/2007 | Christon et al. | |
| 7,241,280 B2 | 7/2007 | Christon et al. | |
| 7,270,651 B2 | 9/2007 | Christon et al. | |
| 7,306,582 B2 | 12/2007 | Christon et al. | |
| 7,311,696 B2 | 12/2007 | Christon et al. | |
| 7,402,157 B2 | 7/2008 | Christon et al. | |
| 7,520,873 B2 | 4/2009 | Sosalla et al. | |
| 7,537,585 B2 | 5/2009 | Christon et al. | |
| 7,632,257 B2 | 12/2009 | Magee et al. | |
| 2002/0000291 A1 | 1/2002 | Coenen et al. | |
| 2003/0114818 A1 | 6/2003 | Benecke et al. | |
| 2004/0170813 A1 | 9/2004 | Digiacomantonio et al. | |
| 2008/0255529 A1 | 10/2008 | Christon et al. | |
| 2008/0255530 A1 | 10/2008 | Christon et al. | |
| 2008/0262454 A1 | 10/2008 | Christon et al. | |

FOREIGN PATENT DOCUMENTS

| | | |
|---|---|---|
| EP | 0 794 280 A2 | 9/1997 |
| EP | 893 115 A2 | 1/1999 |
| EP | 0 934 737 | 8/1999 |
| EP | 0 951 889 A1 | 10/1999 |
| EP | 756 855 B1 | 11/2000 |
| EP | 1 057 465 A1 | 12/2000 |
| EP | 1 117 671 A2 | 7/2001 |
| EP | 776 645 B1 | 3/2002 |
| EP | 1 199 057 A1 | 4/2002 |
| EP | 1 203 571 A2 | 5/2002 |
| EP | 1 117 669 B1 | 1/2003 |
| EP | 1 117 670 B1 | 1/2003 |
| GB | 1070514 | 6/1967 |
| GB | 2 135 568 A | 9/1984 |
| GB | 2 267 024 A | 11/1993 |
| JP | 59-190229 U | 12/1984 |
| JP | 04-218457 A | 8/1992 |
| JP | 05-237146 A | 9/1993 |
| JP | 06-021624 A | 1/1994 |

(56) References Cited

FOREIGN PATENT DOCUMENTS

| | | |
|---|---|---|
| JP | 08-280725 A | 10/1996 |
| WO | WO 94/26221 A1 | 11/1994 |
| WO | WO 96/10380 A2 | 4/1996 |
| WO | WO-99/22688 A1 | 5/1999 |
| WO | WO 99/56690 A1 | 11/1999 |
| WO | WO-00/35401 A1 | 6/2000 |
| WO | WO 00/38915 A1 | 7/2000 |
| WO | WO 01/32318 A2 | 5/2001 |
| WO | WO 01/72252 | 10/2001 |
| WO | WO-01/87212 A1 | 11/2001 |
| WO | WO-03/053313 A2 | 7/2003 |

OTHER PUBLICATIONS

"Multicolored Absorbent Articles: A Brief History," Jeffrey D. Lindsay and Beth A. Lange, Kimberly-Clark Corporation, Neenah, Wisconsin, Published in: IP.com's Prior Art Database, Oct. 10, 2003; Publication ID: IPCOM000019928D, 18 pages.

Depend Regular Absorbency Undergarment Belted, Purchased Oct. 1, 1996, 6 pages.

Serenity Pad for Urine Leakage, Purchased Oct. 11, 1993, 7 pages.

* cited by examiner

DISPOSABLE ABSORBENT ARTICLE DESIGNED TO FACILITATE AN EASY CHANGE

CROSS REFERENCE TO RELATED APPLICATIONS

This application is a continuation of U.S. application Ser. No. 12/824,425, filed Jun. 28, 2010, which is a continuation of U.S. application Ser. No. 11/545,187, filed Oct. 10, 2006, which is a continuation of U.S. application Ser. No. 10/008, 731, filed Dec. 9, 2004, which is a continuation of U.S. application Ser. No. 10/079,184 filed Feb. 20, 2002.

FIELD OF THE INVENTION

This invention is directed to hygienic absorbent articles, such as diapers, training pants and the like. Particularly, the invention is directed to disposable diapers designed to facilitate the process of fitting the diaper to a wearer.

BACKGROUND OF THE INVENTION

Absorbent articles are well known in the art. These articles typically have an absorbent core held or positioned in proximity to the body of a wearer during use by a fastening system in order to capture and absorb bodily exudates discharged from the wearer. Typical absorbent articles include a topsheet facing the wearer, which permits fluid exudates to pass through, and a backsheet, which prevents the exudates from escaping from the absorbent article.

Disposable absorbent articles such as diapers are designed to absorb and contain bodily waste in order to prevent soiling of the body and clothing of the wearer. The disposable diapers typically comprise a single design available in different sizes to fit a variety of wearers ranging from newborns to toddlers undergoing toilet training. The design of the diaper typically affects performance, such as, ability to absorb and contain bodily waste. The size of the diaper typically affects fit, for example, the size of the diaper waist opening, the size of the openings around the thighs, and the length or "pitch" of the diaper.

Articles worn externally to the body of the wearer, such as diapers, are commonly misapplied due to awkward positioning of the wearer or the restless movement of the wearer during fitting. Such misapplication may result in an uneven fit; gaps, which result in leakage; and misplaced parts (such as fasteners), which may result in marking the skin of the wearer and/or discomfort. This is particularly true of caregivers dealing with uncooperative wearers such as babies. Babies, even from a young age, move their legs into awkward positions, roll from side to side, or even violently resist diaper changes using hand and leg motions. As a result, the caregiver often has to hold portions of the wearer's body as well as the diaper during the change process making it very difficult to achieve proper alignment of the diaper for fitting.

Attempts have been made in the art to improve the process of applying an absorbent article to the wearer such as by using an external change aid such as described in co-pending European Patent Application No. 01117671 filed Jul. 26, 2001. The change aids described in said application are devices that assist in the application or removal of articles worn primarily externally on the body of the wearer, especially hygienic absorbent articles, such as diapers, adult incontinence articles, feminine protection articles and the like. However, such external devices are not integrated in the absorbent article itself requiring the caregiver to purchase an extra device Thus, there is a need for a disposable diaper including features that facilitate the changing process. Particularly, there is a need for a diaper having intuitive elements that facilitate a change by enabling a caregiver to get the fit on the wearer right the first time with minimal, if any, adjustment.

There is also a need for a diaper having versatile change elements that enable it to be fitted to a wearer while the wearer is standing or lying down where in either case the diaper can easily be fitted to the wearer without instruction.

SUMMARY

The present invention provides a disposable absorbent article to be worn about the lower torso of a wearer that includes at least one serviceable indicium that facilitates an easy, intuitive change by aligning the article relative to an anatomical feature of the wearer or relative to a component of the article, thus enhancing the fit and corresponding performance of the article. The disposable absorbent article includes a body-facing surface and a garment-facing surface; a longitudinal axis and a transverse axis; a first waist region with a first end edge, a second waist region with a second end edge, and a crotch region interposed therebetween. A pair of opposing longitudinal side edges joins the first end edge and the second end edge. The disposable absorbent article includes a backsheet having a body-facing surface and a garment-facing surface, and a core disposed on the body-facing surface of the backsheet.

Embodiments of the disposable absorbent article include at least one externally visible serviceable indicium disposed on portions of the disposable absorbent article proximate the longitudinal side edges in at least the crotch region. The disposable absorbent article may also include at least one externally visible serviceable indicium disposed on portions of the disposable absorbent article proximate the first and second end edges. The externally visible serviceable indicia distinguish the portions of the garment-facing surface of the article proximate the longitudinal side edges and portions of the article proximate the first and second end edges from a portion of the garment-facing surface of the article proximate an intersection of the longitudinal and transverse axes. For these embodiments, the externally visible serviceable indicia can provide a contoured pattern complementing features of the disposable absorbent article such a shaped core, barrier leg cuffs and/or a fastening system.

For instance, in one embodiment, the disposable article includes a first ear panel disposed along each longitudinal side edge in the second waist region. Each first ear panel includes a body-facing surface and a garment-facing surface. At least a portion of each of the first ear panels includes at least one externally visible serviceable indicium complementing the externally visible serviceable indicium disposed on the garment-facing surface of the article proximate the first and second end edges and/or proximate the longitudinal side edges. For this embodiment, the disposable absorbent article includes a fastening system for releasably securing the first waist region and the second waist region about the lower torso of the wearer. During fitting, the at least one externally visible serviceable indicia on the portion of each of the first ear panels are aligned with the externally visible serviceable indicia proximate the first end edge to form a composite substantially aligned indicia encircling the waist of the wearer. At the same time, the at least one externally visible serviceable indicium on the garment-facing surface of the article proximate the longitudinal side edges form composite substantially aligned indicia encircling the legs of the wearer. The composite substantially aligned indicia encircling the waist and the legs of the wearer denote proper alignment and fit of the article about the hips and legs of the wearer.

Alternate embodiments include at least one internally visible serviceable indicium observable on a portion of the body-facing surface of the disposable absorbent article facilitating the alignment of the article, or components thereof, to anatomic features of the wearer during fitting. For these embodiments the disposable absorbent article may include an elasticized topsheet with an elongated slit opening disposed therein. The elasticized slit opening is intended to align with the wearer's anus and/or genitals to receive fecal matter and/or urine therein. The internally visible serviceable indicia can be used to facilitate such alignment.

In another embodiment, the disposable absorbent article includes a fastening system having separate primary and secondary landing members that attach to tab members during a first fit and a second fit, respectively. The primary and secondary landing members include serviceable indicia providing instructional marks designating matching connections with the tab members during the first fit and the second fit. The first fit provides a loose fit which can enable the article to be maneuvered about the wearer's lower torso during fitting and the second fit provides a secure fit about the wearer's waist.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

Figure 1:
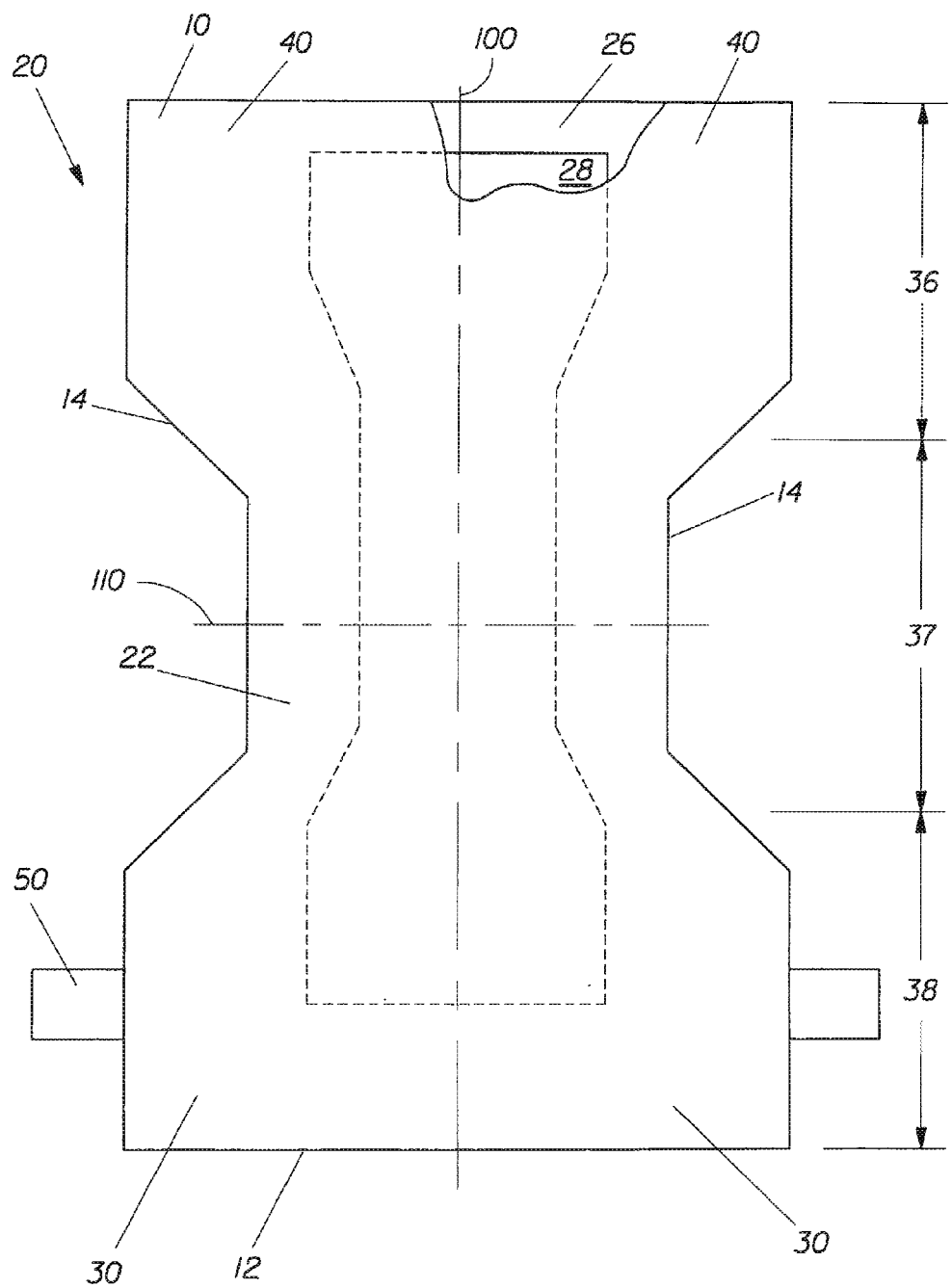
FIG. 1 is a plan view of a disposable absorbent article according to the present invention.

While this specification concludes with claims particularly pointing out and distinctly claiming that which is regarded as the invention, it is anticipated that the invention can be more readily understood through reading the following detailed description of the invention and study of the included drawings.

The present invention provides a disposable absorbent article worn about the lower torso of a wearer including at least one serviceable indicium that facilitates an easy intuitive change. The serviceable indicium is disposed in distinct areas of the article and includes features and/or characteristics signaling to a caregiver and/or wearer how to achieve a proper fit. The wearable article may be applicable to disposable absorbent articles including training pants, incontinence briefs, incontinence undergarments, inserts for disposable or durable diapers or other garments and the like. One embodiment of an absorbent article of the present invention is a unitary disposable absorbent article, such as the disposable diaper 20, shown in FIG. 1.

Definitions

As used herein, the following terms have the following meanings:

"Absorbent article" refers to devices that absorb and contain liquid, and more specifically, refers to devices that are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction and is essentially in the plane of the article when the article is in a flat stretched out position.

The "Z-direction" is orthogonal to both the longitudinal and transverse directions.

The "x-y plane refers to the plane congruent with the longitudinal and transverse directions.

The term "disposable" is used herein to describe absorbent articles that generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "complement" refers to filling in or completing such as by overlapping, matching, or aligning therewith; contextually relating, or highlighting.

As used herein, the term "body-facing surface" generally refers to a surface oriented towards the body when fitted to a wearer.

As used herein, the term "garment-facing surface" generally refers to a surface oriented opposite the body-facing surface when fitted to a wearer.

As used herein, the term "serviceable indicium or indicia" generally refers to distinctive marks, colored regions, patterns, and/or textures disposed on a disposable absorbent article to provide a functional attribute. Particularly, the functional attribute includes providing a visual indication that facilitates an easy intuitive change of the disposable absorbent article during fitting.

As used herein, the term "externally visible", as used in reference to an indicium associated with an article, refers to the ability of a human viewer to visually discern the indicium with the unaided eye (excepting standard corrective lenses adapted to compensate for near-sightedness, farsightedness, or astigmatism) in standard lighting conditions from a point of reference viewing the garment-facing surface of the article while the article is held in a configuration wherein the garment-facing surface is within the field of view.

As used herein, the term "internally visible", as used in reference to an indicium associated with an article, refers to the ability of a human viewer to visually discern the indicium with the unaided eye (excepting standard corrective lenses adapted to compensate for near-sightedness, farsightedness, or astigmatism) in standard lighting conditions from a point of reference viewing the body-facing surface of the article while the article is held in a configuration wherein the body-facing surface is within the field of view.

As used herein, "standard lighting conditions" refer to lighting conditions in which human vision operates efficiently (e.g., the human eye is able to discern complex patterns, shading, and colors). Specifically, for the purposes of describing this invention, standard lighting conditions are at least one of the following:
  a) natural illumination as experienced outdoors during daylight hours,
  b) the illumination of a standard 100 watt incandescent white light bulb at a distance of 2 meters, or
  c) as defined by CIE D65 standard illuminate lighting at 800 lux to a 1964 CIE standard observer.

As used herein, an "anatomic feature" of a wearer may include any externally discernible portion of the wearer's anatomy specific to a certain definable region and/or function. Exemplary anatomic features of human bodies include, without limitation, waste exit ports such as the anus, genitalia, the perineal region, the gluteal groove, leg creases, the navel, buttocks, hip and/or pubic bones, the thighs, the rib cage, and the like.

FIG. 1 is a plan view of the diaper 20 in its flat out, uncontracted state (i.e., without elastic induced contraction) with portions of the structure being cut away to more clearly show the underlying structure of the diaper 20 and with the body-facing portion of the diaper 20 which contacts the wearer facing the viewer. The diaper 20 includes a longitudinal axis 100 and a lateral or transverse axis 110, a first end edge 10 and a second end edge 12 connected by longitudinally extending side edges. A longitudinal side edge refers to an edge oriented ±45° from the longitudinal axis 100 and includes rectilinear and curvilinear side edges. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 generally comprise those portions of the diaper 20 which, when worn, encircle the waist of the wearer. Therefore, the first waist region 36 and the second waist region 38 are commonly referred to as the front waist region and the back waist region, respectively, to correspond to orientation of the diaper 20 relative to the wearer's body during fit. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The chassis 22 of the diaper 20 comprises the main body of the diaper 20. The chassis 22 comprises an outer covering including a liquid pervious topsheet 24 and/or a liquid impervious backsheet 26 and at least a portion of an absorbent core 28 encased between the topsheet 24 and the backsheet 26. For unitary absorbent articles, the chassis 22 comprises the main structure of the diaper 20 with other features added to form the composite diaper structure. While the topsheet 24, the backsheet 26, and the absorbent core 28 may be assembled in a variety of well-known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease, et al. on Dec. 3, 1996; and U.S. Pat. No. 6,004,306 entitled "Absorbent Article With Multi-Directional Extensible Side Panels" issued to Robles et al. on Dec. 21, 1999; each of which is incorporated herein by reference.

The topsheet 24 may be fully or partially elasticized or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein. Further preferred embodiments of elasticized or foreshortened topsheets are described in detail in co-pending European Patent Application No. 01117670 filed Jul. 26, 2001 and copending European Patent Application No. 01117669 filed Jul. 26, 2001 each of which is incorporated by reference herein.

The absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The backsheet 26 is generally that portion of the diaper 20 positioned adjacent the garment-facing surface of the absorbent core 28. Backsheet 26 prevents the exudates absorbed and contained therein from soiling articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by Tredegar, of Richmond, Va. Suitable breathable composite materials comprising polymer blends are available from Clopay Corporation, Cincinnati, Ohio under the name HYTREL blend P18-3097.

The diaper 20 may include a fastening system 50 such as a hook and loop type fastener including at least one engaging component (male fastening component) and at least one landing zone (female fastening component). Alternatively, the fastening system 50 may include a tab and slot type fastener wherein the tab member includes a retaining element that interlocks with an opening such as a slit, slot, or loop.

The diaper 20 may also include side panels, referred to herein as first ear panels 30, disposed in the second waist region 38. The first ear panels 30 may be integral with the chassis 22 comprising extensions of a unibody chassis design or alternatively, the first ear panels 30 may comprise separate members attached to the chassis 22 using adhesives, ultrasonic bonds, radio frequency bonds, or other suitable means. The first ear panels 30 may be elastic or extensible to provide a comfortable and contoured fit by initially conformably fitting the diaper 20 to the wearer and sustaining this fit throughout the time of wear well past when the diaper 20 has been loaded with exudates since the elasticized first ear panels 30 allow the sides of the diaper 20 to expand and contract. The first ear panels 30 may also provide more effective application of the diaper 20 because even if the caregiver pulls one elasticized first ear panel 30 farther than the other during application, the diaper 20 will "self-adjust" during wear. Examples of diapers with elasticized first ear panels are disclosed in U.S. Pat. No. 4,857,067, entitled "Disposable Diaper Having Shined Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 can also include side panels, referred to as second ear panels 40, disposed in the first waist region 36. Similar to the first ear panels 30, the second ear panels 40 may be integral with the chassis 22 comprising extensions of a unibody chassis design or alternatively, the second ear panels 40 may comprise separate members attached to the chassis 22 using adhesives, ultrasonic bonds, radio frequency bonds, or other suitable means. The first and second ear panels 30, 40 may be constructed in any suitable configuration accommodating a particular product design.

An exemplary disposable absorbent article including serviceable indicia for facilitating an easy, intuitive change according to the present invention is the disposable diaper 20 shown in FIGS. 2a-2d. The disposable diaper 20 includes at least one externally visible serviceable indicium 60 that is observable along at least portions of the garment-facing surface of the article proximate the longitudinal side edges 14 in at least the crotch region 37 and also at least one externally visible serviceable indicium 60 along portions of the garment-facing surface of the article proximate the first and second end edges 10, 12 in the first and second waist regions 36, 38, respectively. In each portion, the serviceable indicia are externally visible so as to distinguish portions of the garment facing surface of the article proximate the longitudinal side edges 14 and first and second end edges 10, 12 from a portion of the garment-facing surface of the article proximate the center of the article defined by an intersection of the longitudinal and transverse axes 100, 110. The externally visible serviceable indicia 60 may be disposed directly on the garment-facing surface of the backsheet 26, on the surface of the backsheet 26 opposite the garment-facing surface adjacent to the core 28, on one of the components of the backsheet 26, or beneath the backsheet 26 on underlying layers so long as the indicia are externally visible. The externally visible serviceable indicia 60 may comprise a separate element affixed to a component of the article or may comprise a colorant, such as a dye or ink, applied to a component of the article. In addition, the externally visible serviceable indicia 60 may include a color, a pattern, and/or a texture that distinguish the designated portions from the center portion of the article.

For externally visible serviceable indicia comprising a pattern, the pattern may be in the form of a series of shapes and/or images. For example, the pattern may be formed of one or more dots, one or more lines, one or more regular or irregular shapes (such as circles, ellipses, diamonds, squares, and the like), or combinations thereof. Alternatively, a pattern may be in the form of a variation of color along a length of the serviceable indicia. For example, the color may vary from light to dark or from one hue to another. Images may include drawings of characters or objects readily recognizable to children.

For serviceable indicia comprising texture, portions of the backsheet 26 may be mechanically treated to provide texture by methods known in the art, including mechanical operations, such as pleating, corrugating, or ring rolling to provide folds that are able to open when the backsheet 26 is extended in a direction generally orthogonal to the pleats or folds. In addition to providing texture, these mechanical operations may also provide extensibility. Suitable processes for ring rolling or pre-corrugating, including extensible webs made thereby, are described in U.S. Pat. No. 4,107,364 issued to Sisson on Aug. 15, 1978; U.S. Pat. No. 4,834,741 issued to Sabee on May 30, 1989; U.S. Pat. No. 5,167,897 issued to Weber et al. on Dec. 1, 1992, and U.S. Pat. No. 5,702,382 issued to Osborn, III et al. on Dec. 30, 1997, each of which are hereby incorporated herein by reference.

Alternatively, serviceable indicia comprising texture may be accomplished by forming a strainable network having at least two contiguous, distinct, and dissimilar regions. Films thus formed have in the past been termed structural elastic-like films ("SELF"). A structural elastic-like film or web is an extensible material that can exhibit an elastic-like behavior in the direction of elongation without the use of added elastic materials. However, SELF webs can be made which exhibit little elastic behavior. In particular, webs comprising a laminate of films and nonwovens can be made which exhibit little elastic behavior beyond very low levels of strain.

Serviceable indicia comprising SELF suitable for the present invention, and methods of forming SELF webs suitable for use as backsheets 26, are more completely described in U.S. Pat. No. 5,518,801 entitled Web Materials Exhibiting Elastic-Like Behavior, issued to Chappell, et, al. on May 21, 1996; U.S. Pat. No. 5,650,214 entitled Web Materials Exhibiting Elastic-Like Behavior and Soft, Cloth-like Texture, issued to Anderson et al. on Jul. 22, 1997; and U.S. Pat. No. 5,904,673 entitled Absorbent Article with Structural Elastic-like Film Web Waist Belt, issued to Roe et al. on May 18, 1999, all of which are hereby incorporated herein by reference. For film/nonwoven laminate backsheets, the processes described in the above-mentioned patents can be performed on the laminate material or on the separate components prior to lamination, or both.

Figure 2A:
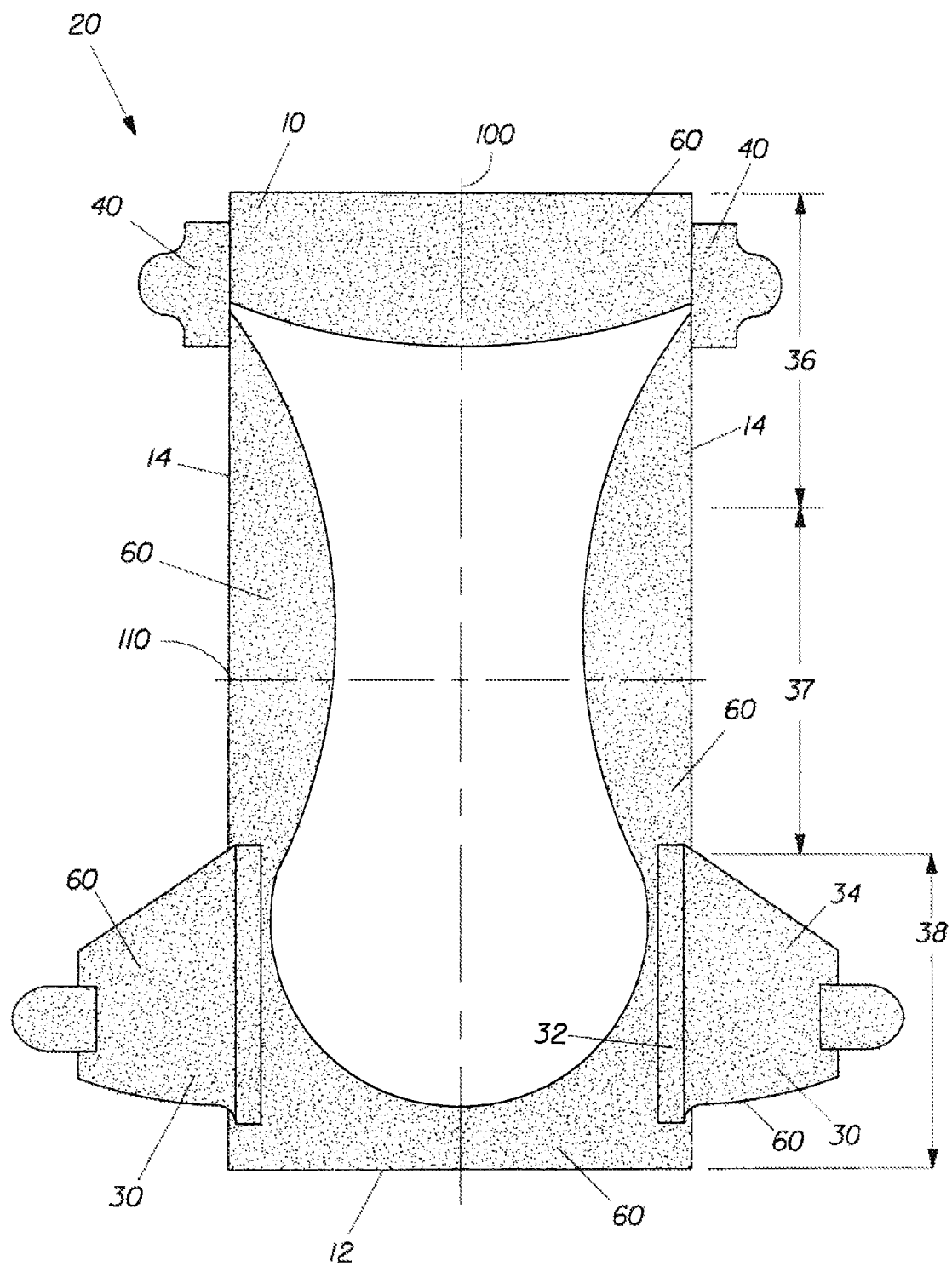
FIG. 2a is a plan view of a disposable absorbent article according to the present invention including externally visible serviceable indicia disposed on the garment-facing surface of the article.

For the embodiment shown in FIG. 2a, the first ear panels 30 disposed along each of the longitudinal side edges 14 in the second waist region 38, include a body-facing surface and a garment-facing surface, a proximal edge 32 joined to the longitudinal side edge 14 and a distal edge 34 opposite the proximal edge 32. At least a portion of each of the first ear panels 30 includes at least one externally visible serviceable indicium 60 complementing the externally visible serviceable indicia 60 disposed on the garment-facing surface of the article proximate the first end edge 10, the second end edge 12 and/or proximate the longitudinal side edges 14. Like the externally visible serviceable indicia 60 externally observable on the garment-facing surface of the article, the at least one externally visible serviceable indicium 60 on the first ear panels 30 are also externally visible as described above.

Figure 2B:
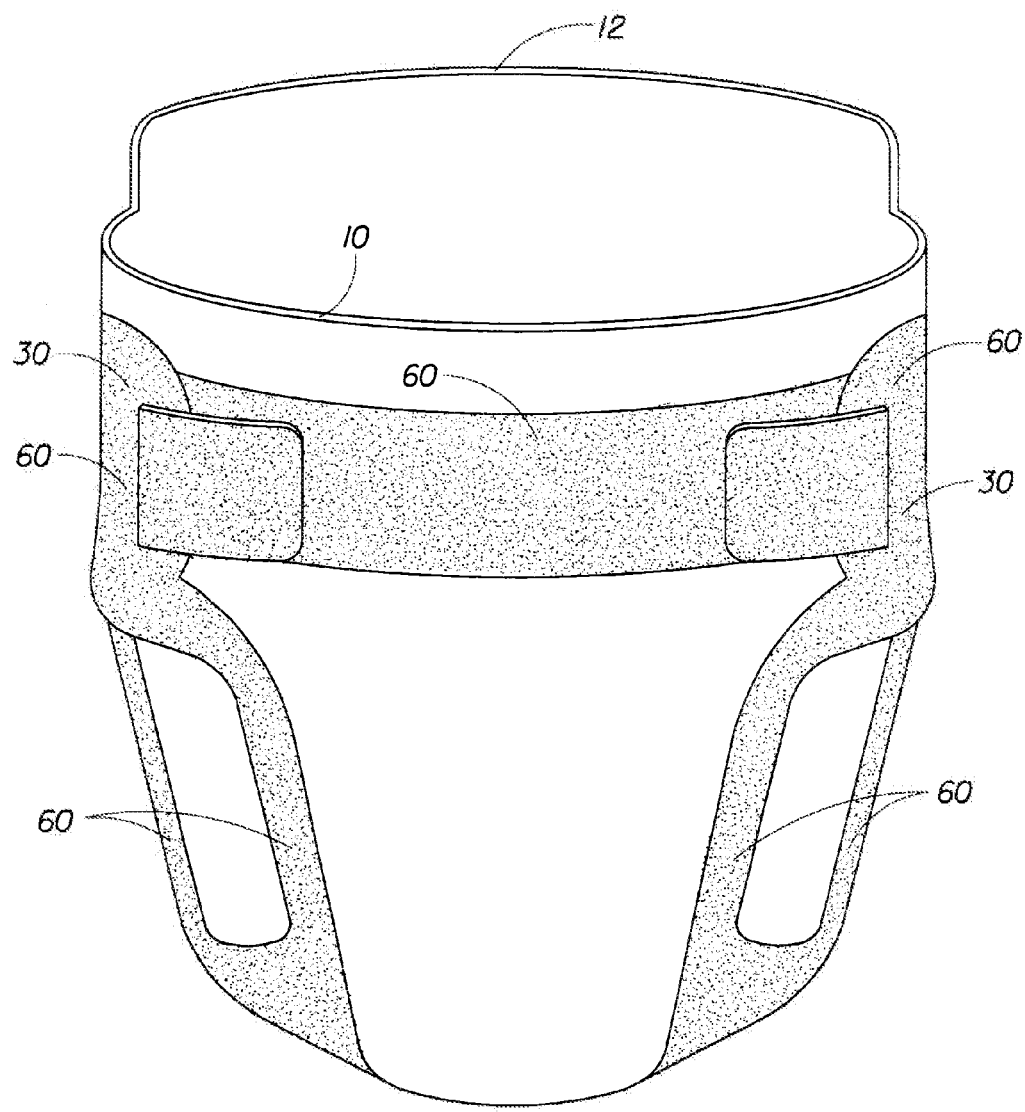
FIG. 2b is a three dimensional front view of the disposable absorbent article depicted in FIG. 2a showing the first waist region attached to the second waist region.
Figure 2C:
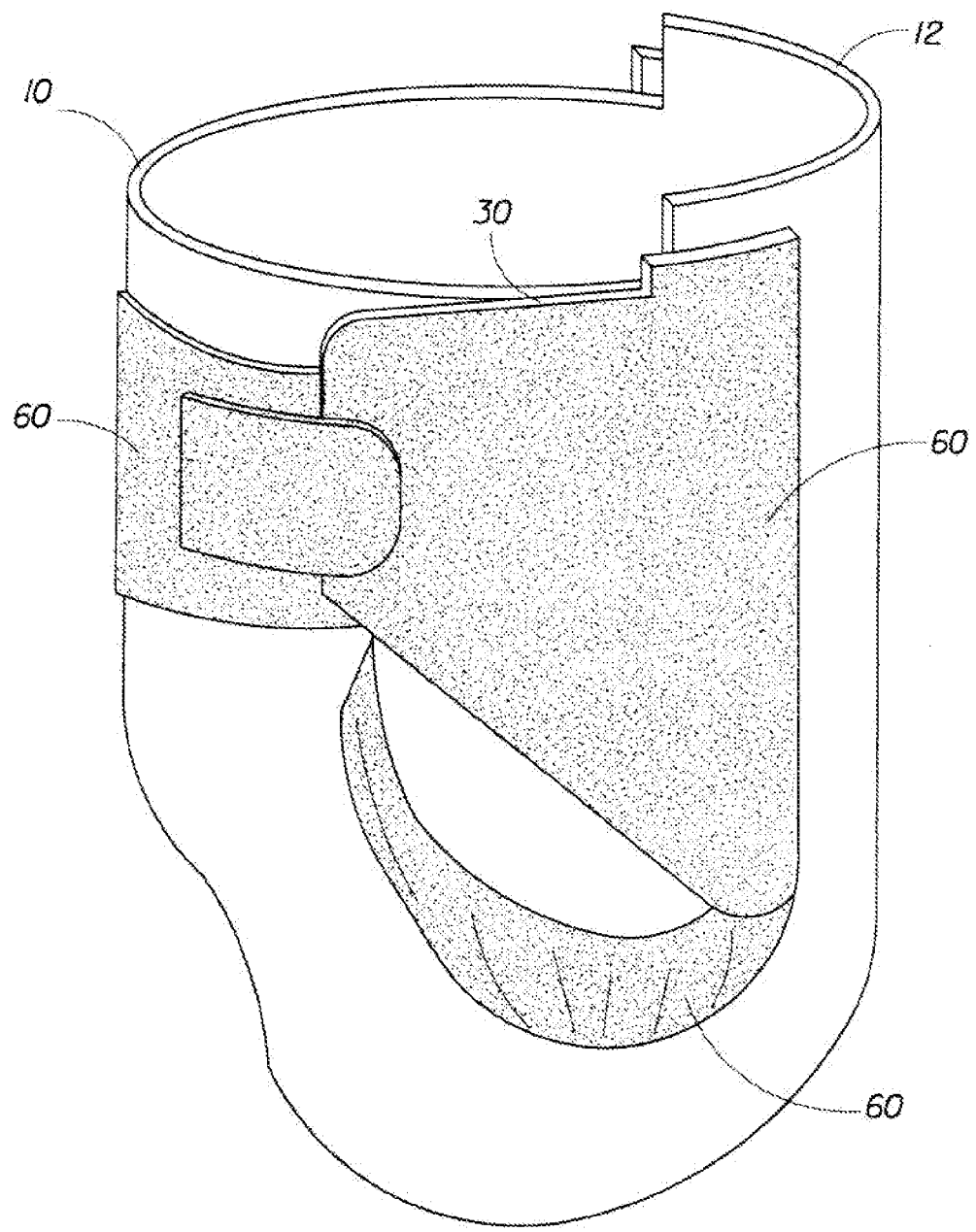
FIG. 2c is a three dimensional side view of the disposable absorbent article depicted in FIG. 2a showing the first waist region attached to the second waist region.
Figure 2D:
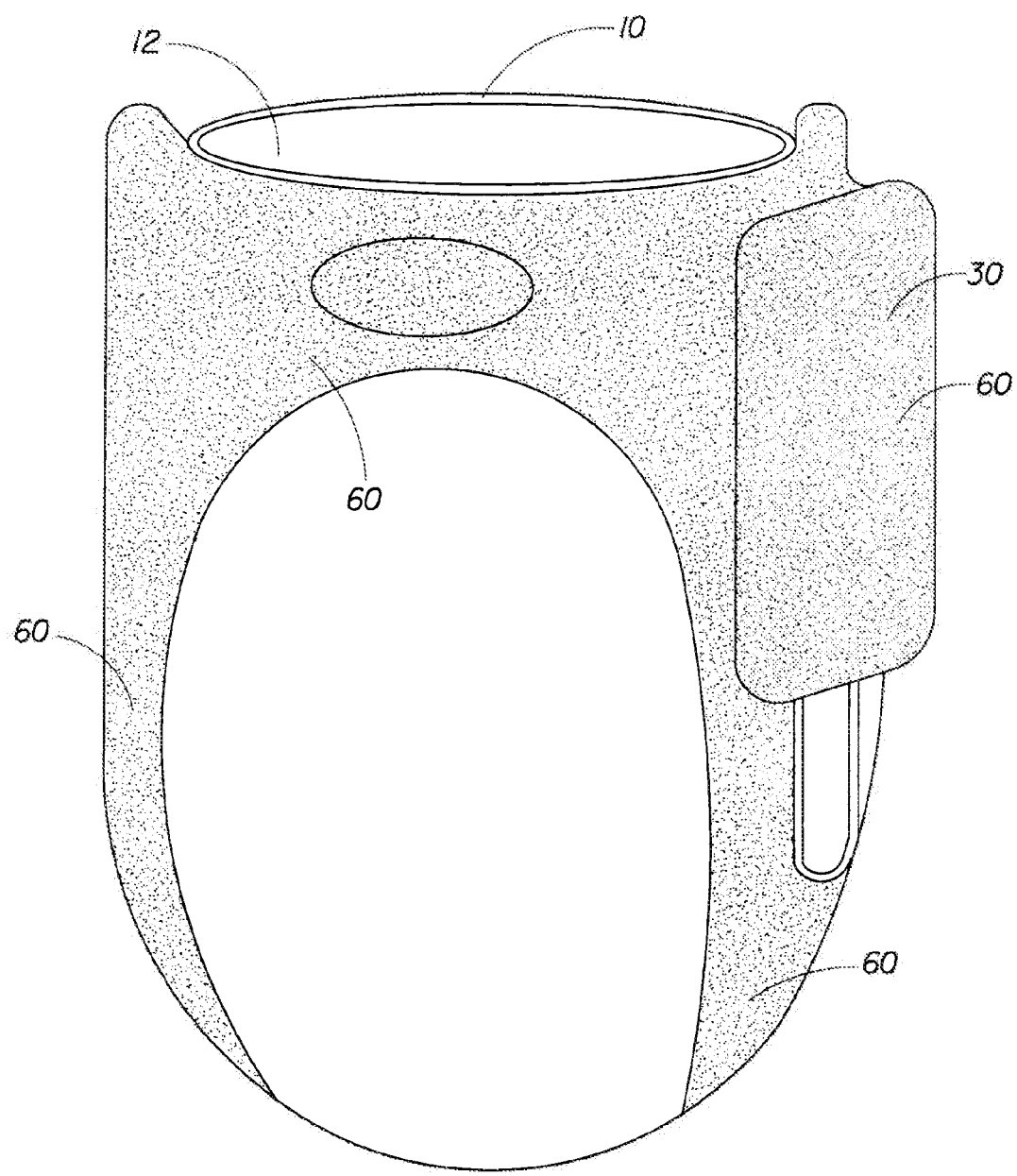
FIG. 2d is a three dimensional rear view of the disposable absorbent article depicted in FIG. 2a showing the first waist region attached to the second waist region.

Once the article is fitted to the wearer, the externally visible serviceable indicium 60 on the garment-facing surface of the first ear panels 30 and the externally visible serviceable indicium 60 on the portion of garment-facing surface of the article near the first end edge 10 facilitate as well as accentuate the fastening system 50 by forming a composite substantially aligned indicium appearing, in one non-limiting embodiment illustrated in FIGS. 2b-2d, as a band encircling the waist of the wearer. Alternatively, the externally visible serviceable indicia 60 form a partially overlapping or aligned composite indicium as the article is fitted to a wearer. At the same time, the externally visible serviceable indicia 60 disposed on the portions of the garment-facing surface of the article along the longitudinal side edges 14 encircle the legs of the wearer in a substantially overlapping and aligned manner, forming a composite substantially aligned indicium appearing, for example, as a continuous band around each of the wearer's legs as illustrated in FIG. 2c.

Figure 3:
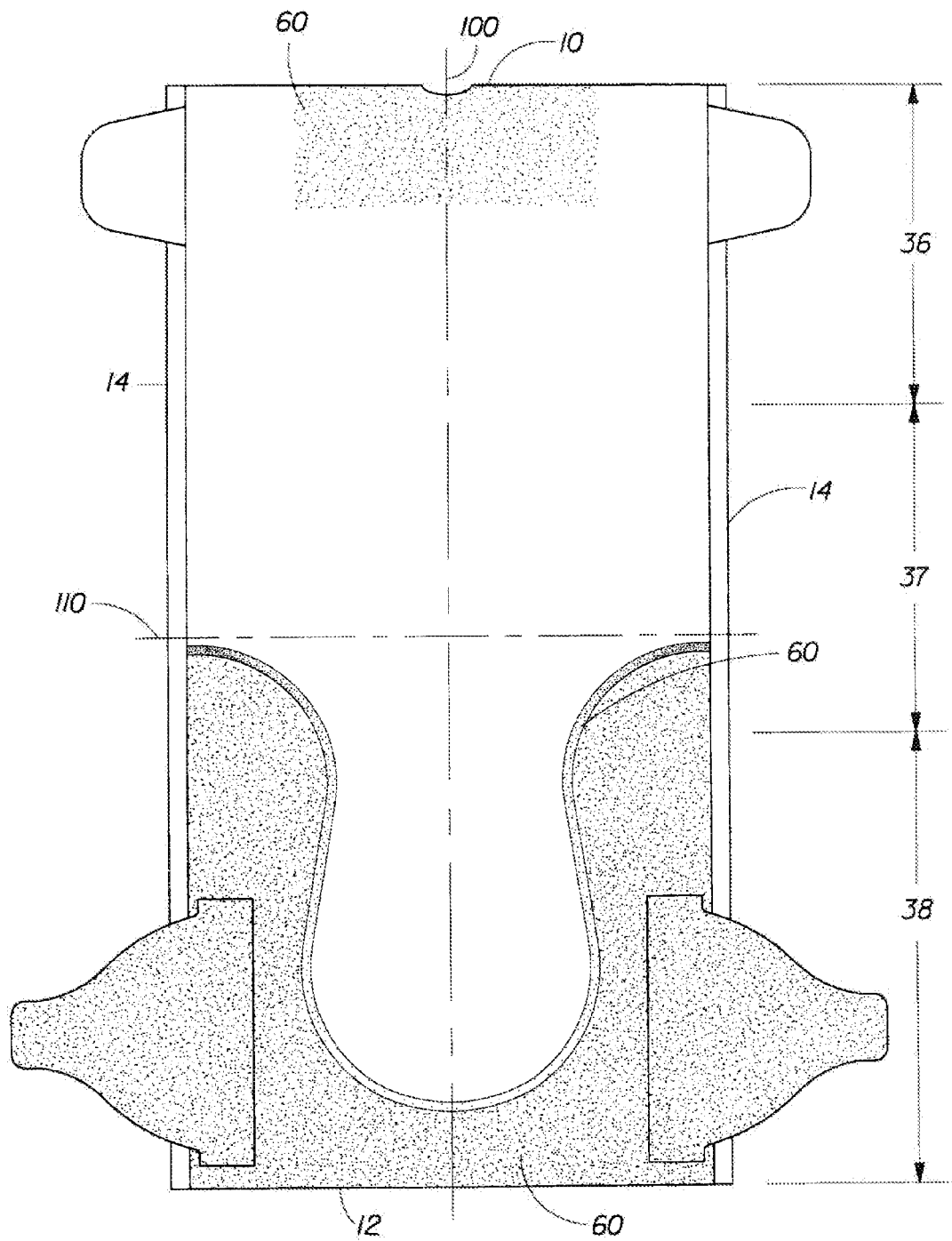
FIG. 3 is a plan view of a disposable absorbent article according to the present invention including externally visible serviceable indicia in the rear waist region providing a contoured pattern.

For this embodiment, the externally visible serviceable indicia 60 on portions of the garment-facing surface of the article proximate the longitudinal side edges 14 and the externally visible serviceable indicia 60 proximate the first and second end edges 10, 12 can be made to form a contoured pattern that distinguishes the first waist region 36 from the second waist region 38. At the same time, the contoured pattern can be made to complement the wearer's anatomy. For instance, the contoured pattern for the embodiment shown in FIG. 3 is curvilinear such that the pattern in the second waist region 38 and a portion of the crotch region 37 is concave relative to the intersection of the longitudinal and transverse axes 100, 110. Such concave curvilinear pattern can be made to complement the wearer's buttocks. Alternatively or else in addition to the pattern in the second waist region 38, the pattern in the first waist region 36 and a portion of the crotch region 37 can be convex relative to the intersection of the longitudinal and transverse axes 100, 110 as shown in FIG. 2a. Such convex pattern, particularly the pattern proximate the first end edge 10, can complement the shape of the wearer's belly.

Figure 4:
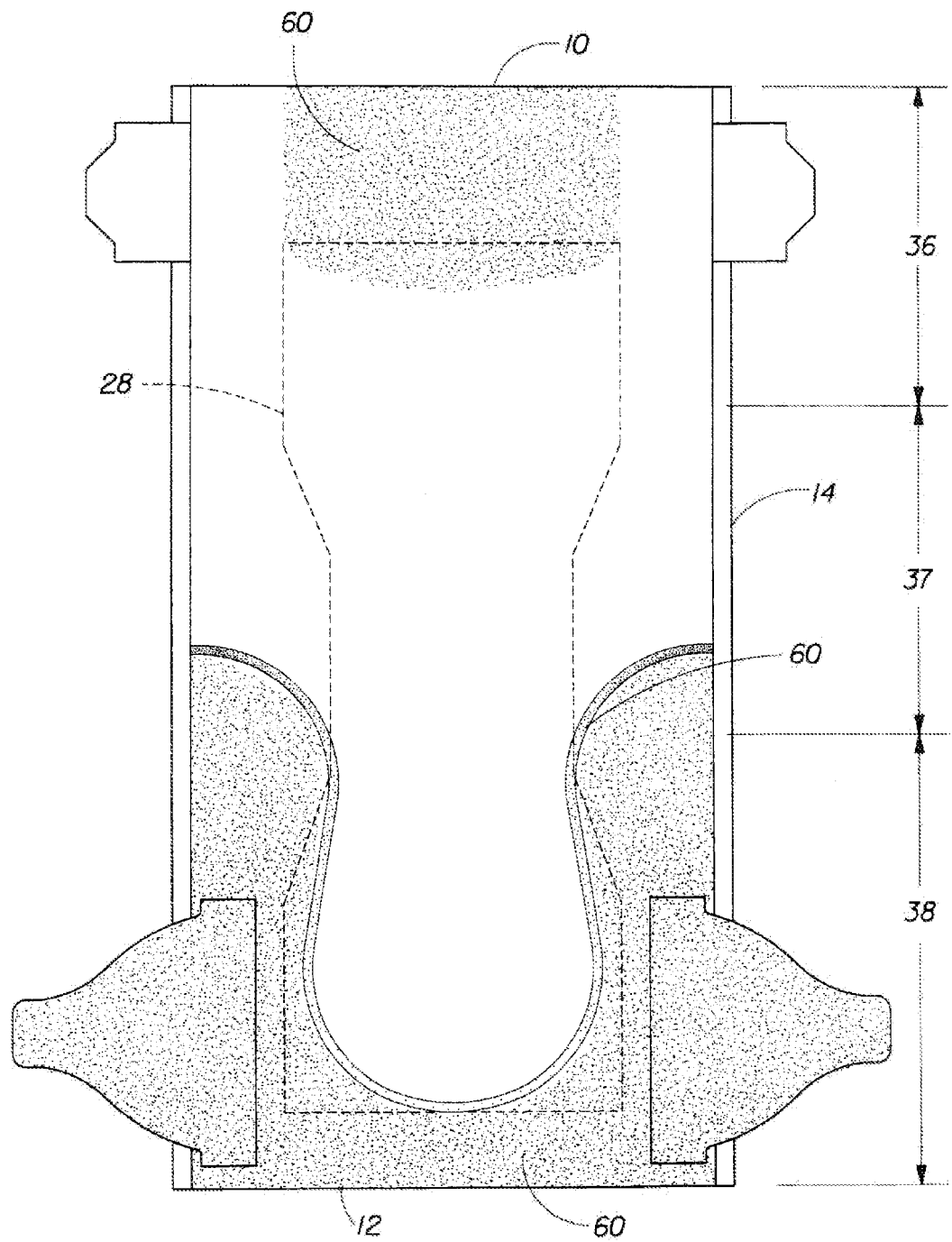
FIG. 4 is a plan view of a disposable absorbent article according to the present invention including externally visible serviceable indicia in the rear waist region providing a contoured pattern complementing the shape of the core.

In addition to accommodating the fastening system 50 and particularly the fit of the diaper 20, the contoured pattern formed by the externally visible serviceable indicia 60 can be made to accentuate other features of the disposable absorbent article such as the absorbent core, the gasketing leg cuffs, or the barrier leg cuffs. For instance, the absorbent core 28 may have an hourglass shape design having a narrow portion in the crotch region 37 to improve the overall fit of the diaper 20. Additionally, the core 28 may comprise one or more rounded or otherwise shaped ends. As shown in FIG. 4, the contoured shape formed by one or more externally visible serviceable indicia 60 may complement or highlight the actual core shape or an idealized core shape (e.g., such as an idealized core shape having rounded ends on a diaper having a core with rectangular ends as illustrated in FIG. 4), making it more appealing to the consumer. In addition, the contoured pattern matching the core shape can provide a visual signal indicating proper alignment of the diaper 20 with respect to the wearer's lower torso, i.e., in the lateral direction, enhancing the fit of the diaper 20 in the wearer's crotch region 37, thus improving the overall performance of the diaper 20. On the other hand, the contoured pattern disposed on the garment-facing surface of the article may align with the barrier cuffs or gasketing leg cuffs disposed on the body-facing surface of the disposable absorbent article, accenting the articles ability to prevent leakage. In some of these embodiments, only externally visible serviceable indicia 60 proximate the longitudinal side edges 14 and/or proximate one of the end edges 10, 12, e.g., the second end edge 12 proximate the second waist region 38, may be required to accentuate the absorbent core 28 and facilitate lateral alignment of the article with respect to the wearer's anatomy.

In certain embodiments, the externally visible serviceable indicia 60 may be sufficiently opaque, or have a sufficiently dark color, to additionally provide a masking benefit, effectively preventing visual detection of a layer, material, or substance underlying the serviceable indicia. For example, the externally visible serviceable indicia 60 proximate the longitudinal side edges 14 of a diaper 20 may have an opacity such that feces and/or portions of the absorbent core 28 that may be present under the region of the backsheet 26 proximate the longitudinal side edges 14 of the diaper 20 are not visible from outside the diaper 20.

In certain preferred embodiments, disposable absorbent article can include instructional serviceable indicia 70 providing guidance or instruction to the caregiver relative to the tightness of fit of the article about the wearer. In particular, the instructional serviceable indicia 70 can indicate to the caregiver whether to adjust the fit or switch to a different size diaper in which proper fit can be obtained. For example, instructional serviceable indicia 70 can be disposed on the garment facing surface of the article matching instructional serviceable indicia 70 on the garment facing surface of the first ear panels 30 to provide an indication that the first ear panels 30 either do not sufficiently overlap the first waist region 36 indicating a loose fit, or overlap the first waist region 36 too far indicating an uncomfortably tight fit. In particular, too little an overlap may result in overly loose leg fit while too great an overlap may result in overly tight leg fit.

Figure 5:
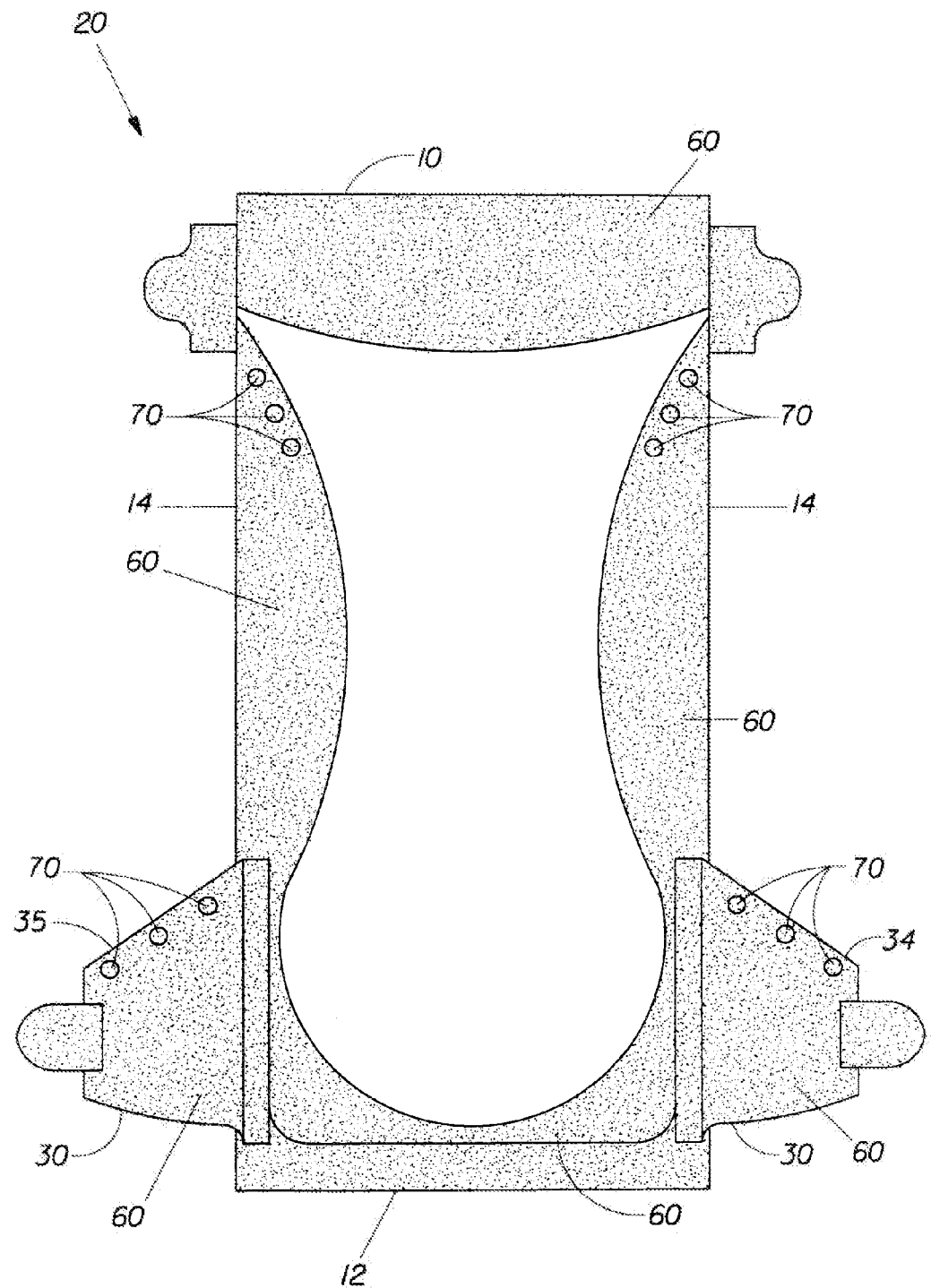
FIG. 5 is a plan view of the disposable absorbent article depicted in FIG. 2a including instructional serviceable indicia providing guidance or instruction to the caregiver relative to tightness of fit of the article about the wearer.

Preferably, the instructional serviceable indicia 70 are disposed proximate the longitudinal side edges 14 of the article for at least a portion of the longitudinal side edge 14 and proximate the inner edge 35 of the first ear panel 30 for at least a portion of the inner edge 35 as shown in FIG. 5. The instructional serviceable indicia 70 providing guidance or instruction to the caregiver relative to the tightness of fit may include dots, graphics of characters, numbers, line segments, and/or patterns.

In an alternate non-limiting embodiment, the disposable absorbent article has a body-facing surface including portions thereof having at least one internally visible serviceable indicium 80. The internally visible serviceable indicium 80 may facilitate an easy, intuitive change by providing a guide for aligning the wearer with the article during fitting so that in turn the wearer is accurately placed on the article for fastening, requiring minimal adjustment.

Figure 6:
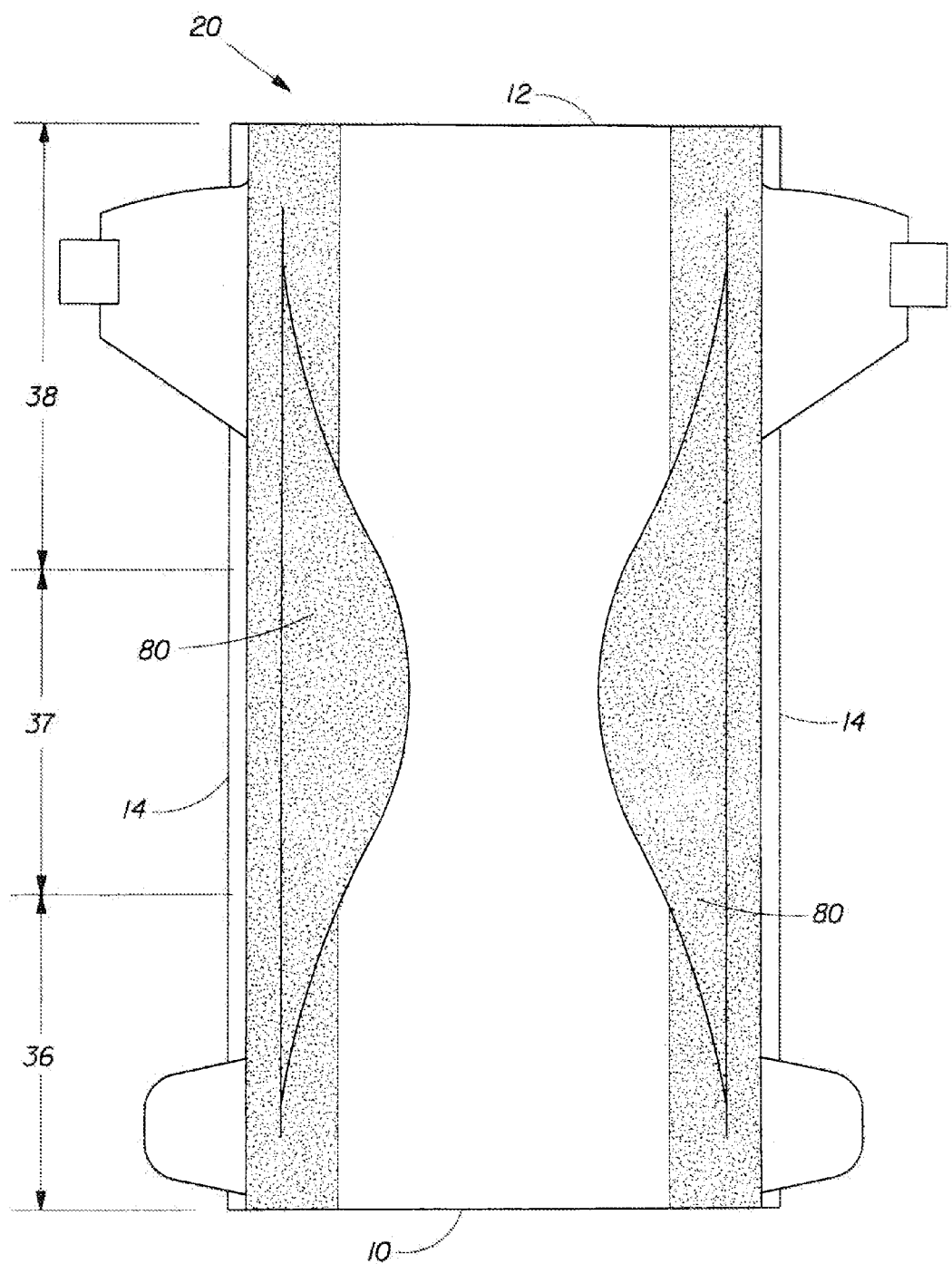
FIG. 6 is a plan view of the body-facing surface of the disposable absorbent article according to the present invention including internally visible serviceable indicia.
Figure 7:
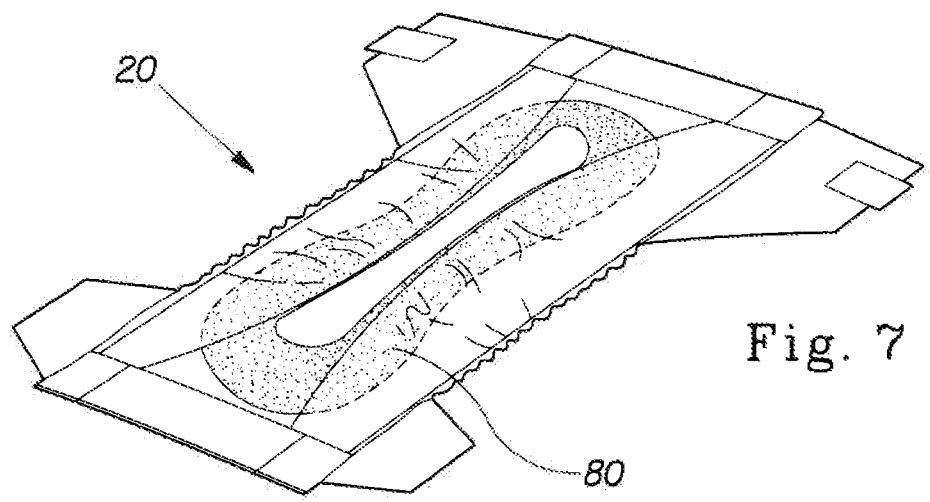
FIG. 7 is a plan view of the body-facing surface of the disposable absorbent article according to the present invention including an internally visible serviceable indicium, which is both colored and 3-dimensional.
Figure 8:
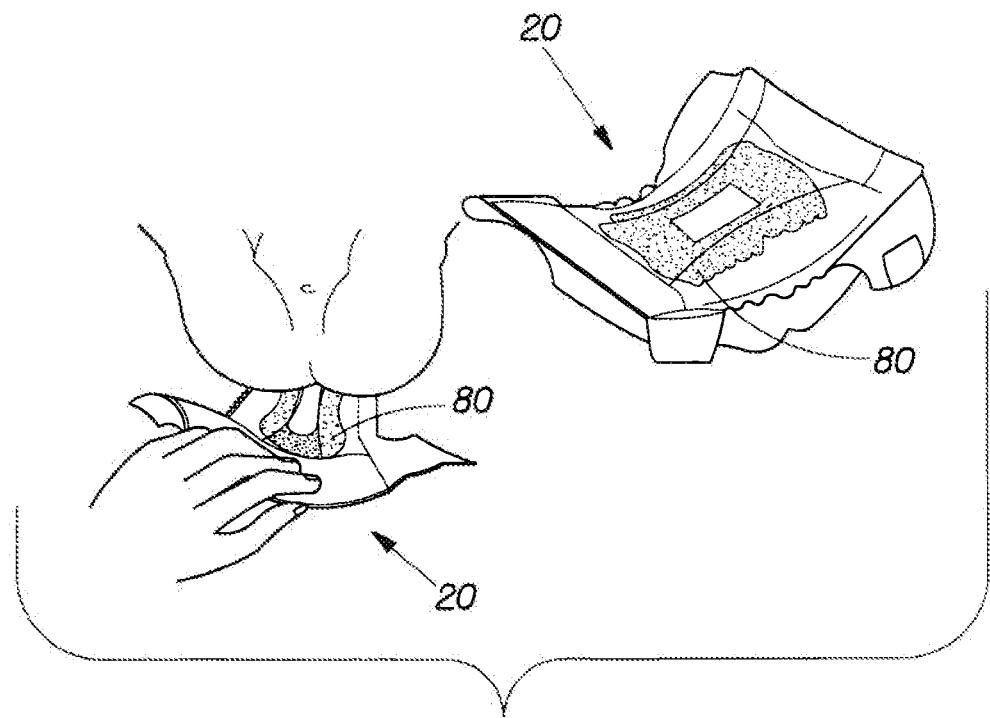
FIG. 8 shows the disposable absorbent article depicted in FIG. 7 being fitted to a wearer.

In certain non-limiting embodiments, the internally visible serviceable indicia 80 can be disposed on the body-facing surface of the article to facilitate the placement or alignment of the article, or a component thereof, with respect to the lateral axis 110 and/or longitudinal axis 100 of the article with an anatomic feature of the wearer. For instance, the topsheet 24 of the article may comprise an internally visible serviceable indicium 80, such as a mark in the crotch region 37, that, when aligned to the anus, results in improved fit and waste containment performance of the article. In an embodiment shown in FIG. 6, the internally visible serviceable indicium 80 is visible on the body-facing side of diaper 20 identifying the crotch area to aid in longitudinal positioning. In the embodiment shown in FIG. 7, the internally visible serviceable indicium 80 is colored and includes a three dimensional contour to facilitate alignment of the article with the wearer during fitting as shown in FIG. 8.

Similar to the embodiments including externally visible serviceable indicia 60, the internally visible serviceable indicia 80 may include a color, a pattern, and/or a texture that distinguish the designated portions of the body-facing surface of the article from other regions of the body-facing surface not comprising the internally visible serviceable indicia 80. The internally visible serviceable indicia 80 may be associated with any portion or component of the article visible on or through the body-contacting surface of the article, including the topsheet 24, the absorbent core 28 or portions thereof, the fastening system 50, the topsheet 24, and the backsheet 26. In additional embodiments, the internally visible serviceable indicia 80 may be disposed proximate the longitudinal side edges 14 and proximate the first and second end edges 10, 12 of the article to provide a contoured pattern distinguishing the first waist region 36 from the second waist region 38. The contoured pattern can be made to complement the wearer's anatomy indicating to the caregiver where to place the wearer during fitting. For instance, internally visible serviceable indicia 80 can form a curvilinear pattern such that the pattern in the second waist region 38 is concave relative to the longitudinal and transverse axes 100, 110 in order to match the contours of the wearer' buttocks. The pattern in the first waist region 36 can also be curvilinear relative to the longitudinal and transverse axes 100, 110 or else linear, but in either case, contoured to match the sides of the wearer's lower back. As a result, the contoured pattern can be produced to provide an imprint of a wearer's lower back and buttocks region on the body-facing surface of the article directing the caregiver where to place the wearer during fitting.

As described above for externally visible serviceable indicia 60, the internally visible serviceable indicia 80 may be disposed on the body-facing surface of the topsheet 24 or beneath the topsheet 24 as long as it is visible from the body-facing surface. In addition, the internally visible serviceable indicia 80 can have different colors, color patterns, gradient patterns, or textures used in order to communicate softness of the article towards the body and also provide some opacity sufficient to mask any underlying layer or material, thereby preventing the visual discernment of the layer, material, or substance through the serviceable indicia.

In some preferred embodiments comprising an elastically foreshortened top sheet 24 having a hole or slit 90 adapted to allow feces to pass to the underside of the topsheet 24, such as those described above and in detail in copending patent application Ser. No. 01117670 filed Jul. 26, 2001 and copending European Patent Application No. 01117669 filed Jul. 26, 2001, the internally visible serviceable indicia 80 on the body-facing surface of the article may facilitate alignment of the hole or slit 90 with the anus and/or gluteal groove. In these embodiments, the internally visible serviceable indicia 80 may comprise colored regions on the body-facing surface of the article along the longitudinal and/or lateral edges of the hole or slit 90.

Figure 9:
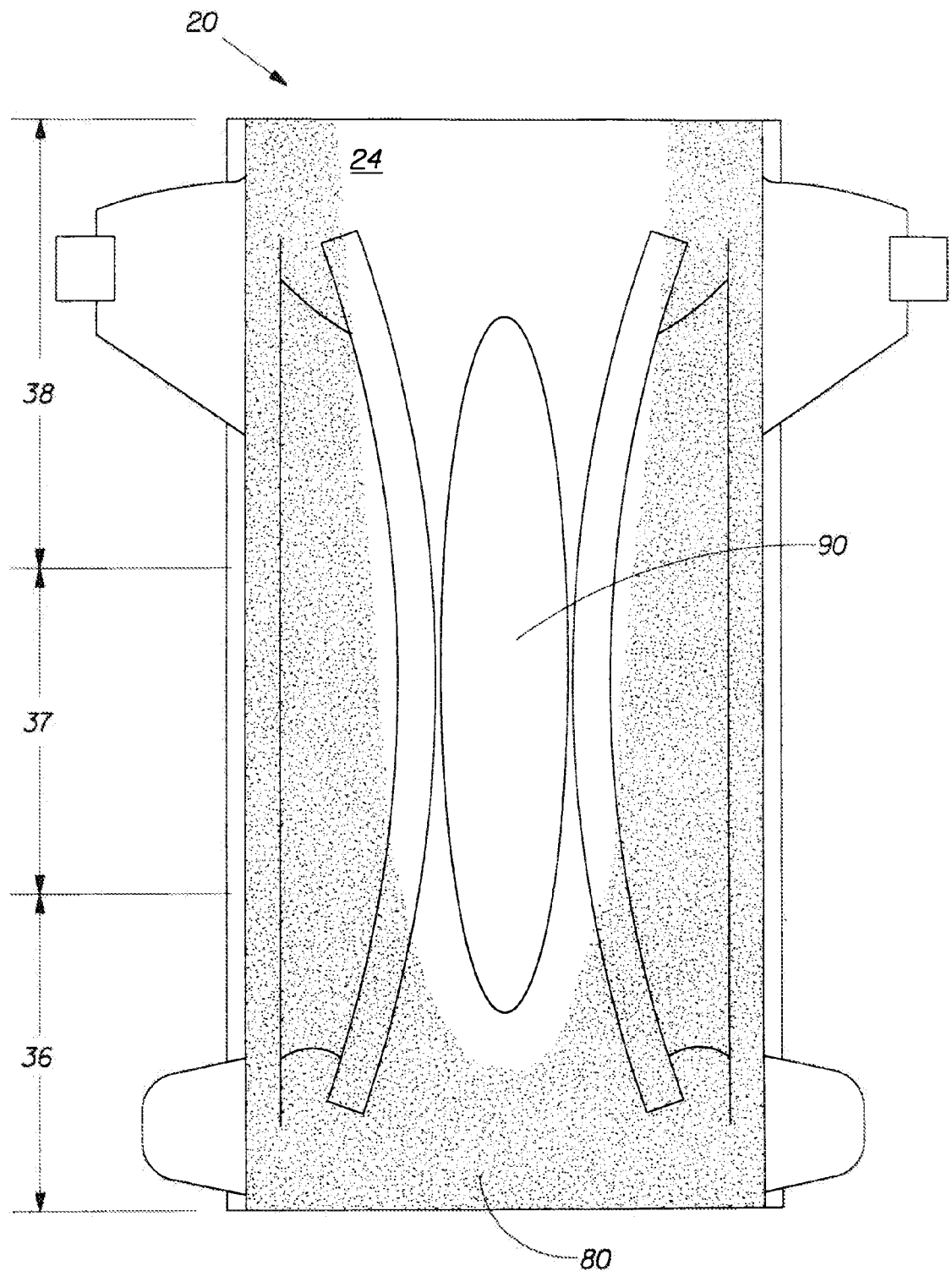
FIG. 9 is a plan view of the body-facing surface of the disposable absorbent article according to the present invention including an elastically foreshortened topsheet and a slit opening with visible serviceable indicia highlighting the first waist region of the article with a smooth curved transition towards the back.
Figure 10:
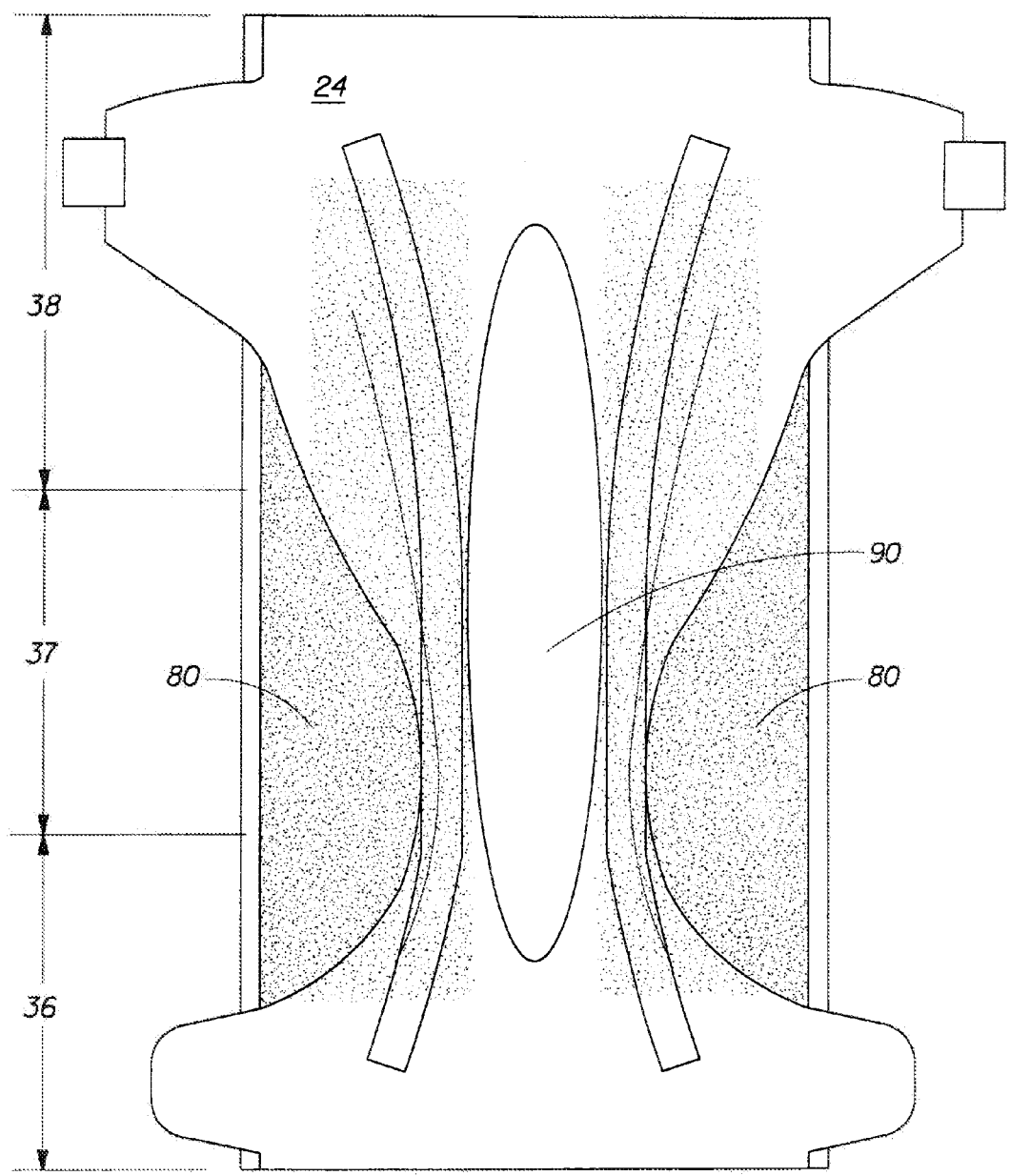
FIG. 10 is a plan view of the body-facing surface of the disposable absorbent article according to the present invention including an elastically foreshortened topsheet and a slit opening with visible serviceable indicia highlighting the crotch region of the article.
Figure 11:
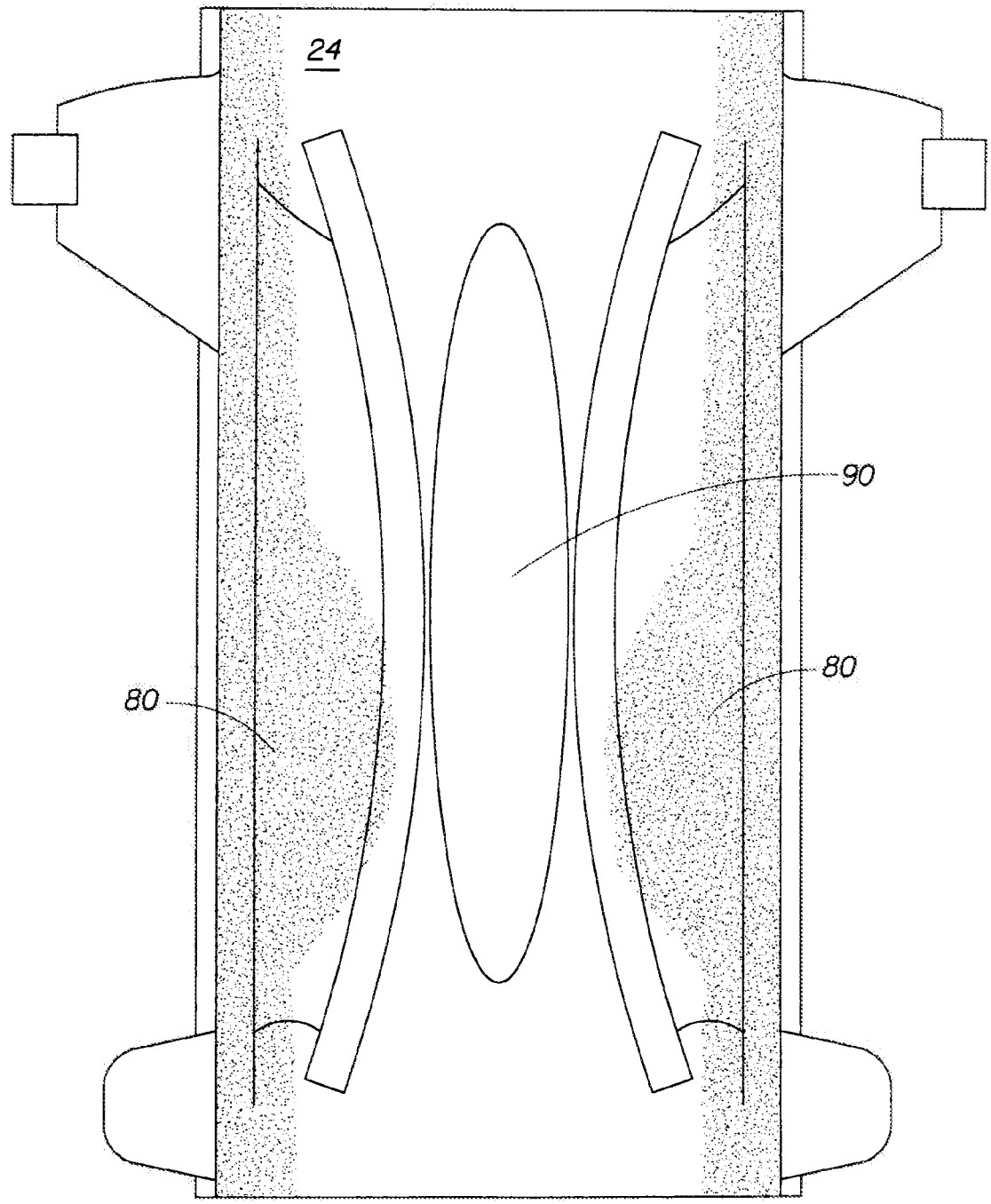
FIG. 11 is a plan view of the body-facing surface of the disposable absorbent article according to the present invention including an elastically foreshortened topsheet and a slit opening with visible serviceable indicia highlighting crotch region of the article and the position of the slit opening.

In an embodiment shown in FIG. 9, the diaper 20 includes an elastically foreshortened topsheet 24 having a hole 90 adapted to allow feces to pass to the underside of the topsheet 24. In this particular embodiment, the internally visible serviceable indicium 80 highlights the front region of the article with a smooth curved transition towards the back aiming at better positioning of the article in the longitudinal direction. In addition, the curvature of the colored indicia in the back provides for improved transverse positioning of the hole 90 in relation to the anus. The embodiment shown in FIG. 10 is similar to the embodiment in FIG. 9 in that the internally visible serviceable indicia 80 identifies the crotch area of the article and also aids in positioning of the hole 90 in the topsheet 24 relative to the anus.

Other diaper embodiments including internally visible serviceable indicia 80 for aligning the hole or slit 90 in an elasticized topsheet 24 with the anus of the wearer are shown in FIGS. 11-18. For the embodiment shown in FIG. 11, a diaper 20 comprising an elastically foreshortened topsheet 24 includes internally visible serviceable indicia 80 identifying the crotch area of the diaper 20 and also the position of the hole 90 in the topsheet 24 relative to the anus.

Figure 12:
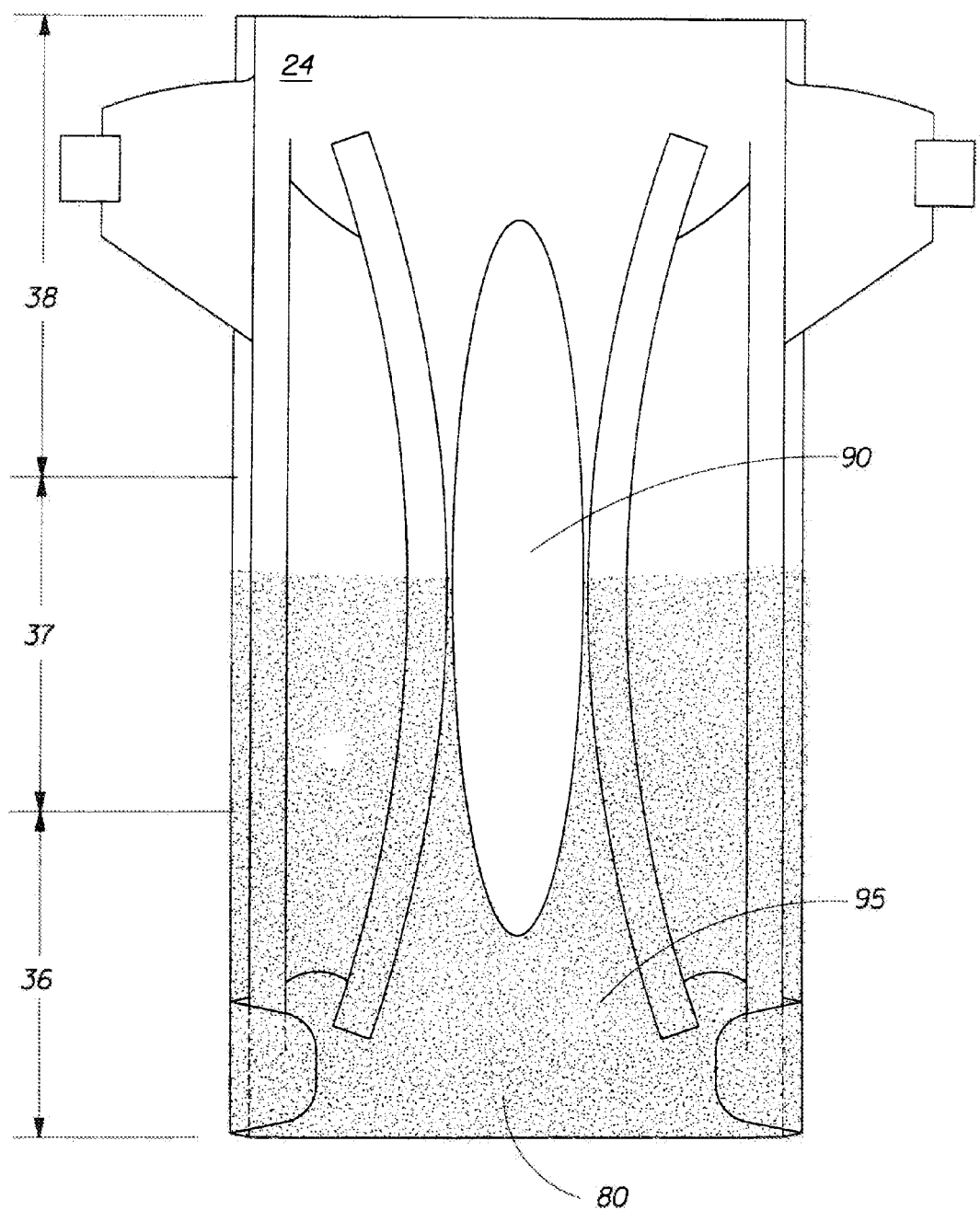
FIG. 12 is a plan view of the body-facing surface of the disposable absorbent article according to the present invention including an elastically foreshortened topsheet and a slit opening with visible serviceable indicia highlighting the first waist region of the article.
Figure 13:
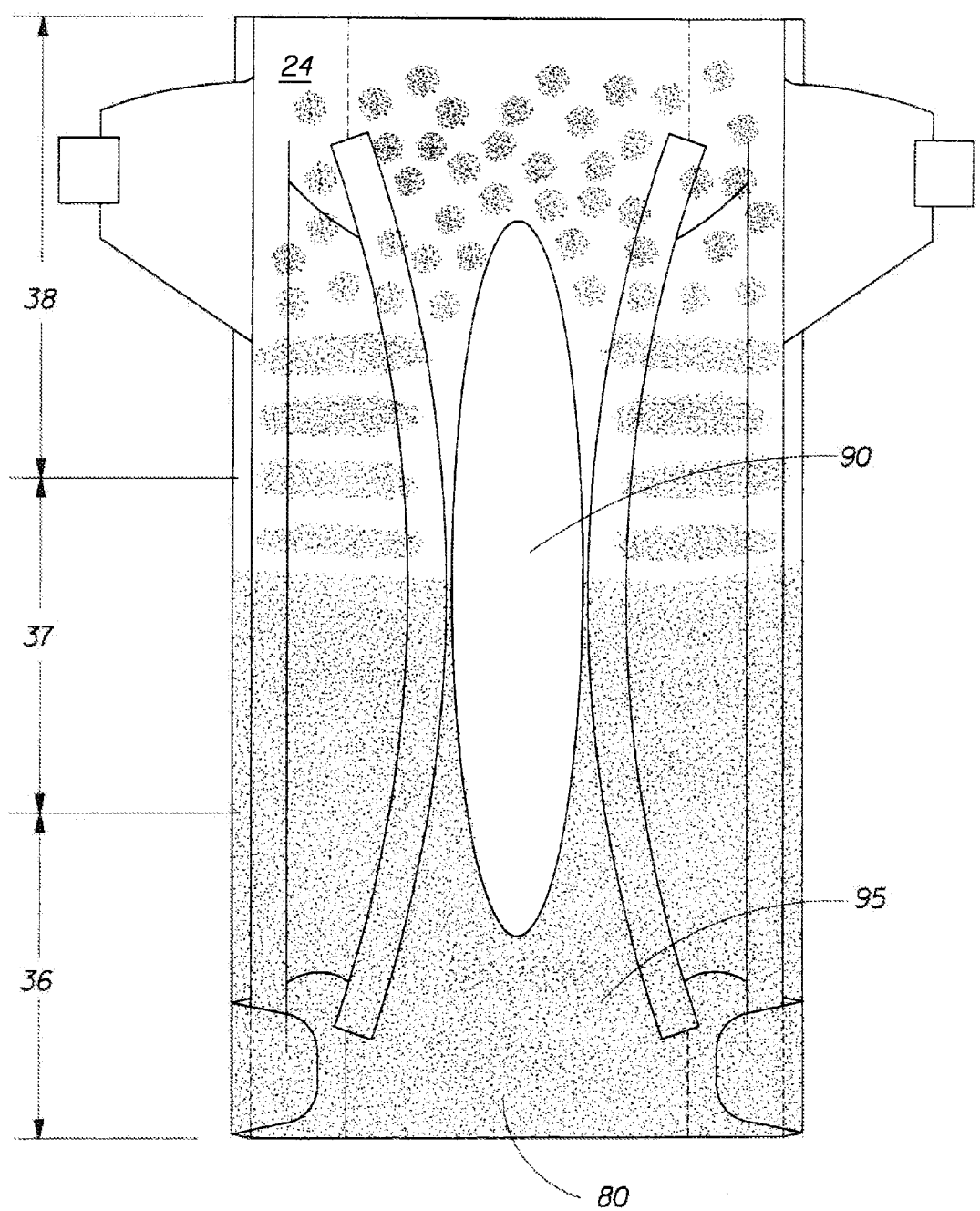
FIG. 13 is a plan view of the body-facing surface of the disposable absorbent article depicted in FIG. 12 with visible serviceable indicia providing patterns to create a smooth transition between the first waist region and the second waist region of the article.
Figure 14:
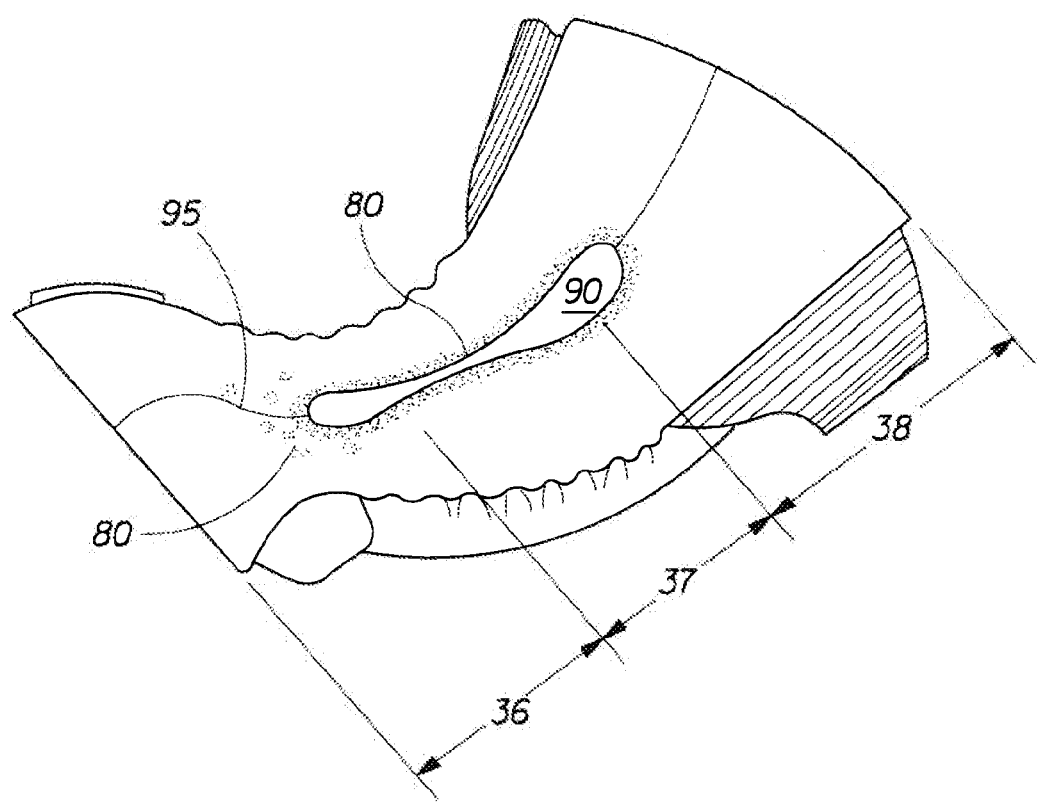
FIG. 14 is a plan view of the body-facing surface of the disposable absorbent article according to the present invention including an elastically foreshortened topsheet and a slit opening with visible serviceable indicia highlighting the slit area and a target urination zone in the first waist region.

FIG. 12 shows an alternative embodiment of internally visible serviceable indicia 80 on the body-facing side of an article having an elastically foreshortened topsheet 24 with the internally visible indicia identifying the front waist region of the diaper 20 and highlighting a target urination zone 95 therein that is particularly applicable for male wearers. FIG. 13 shows an embodiment similar to the embodiment in FIG. 12, with a gradient color and patterns to create a smoother transition between front and back of the article. A further embodiment is shown in FIG. 14, where internally visible serviceable indicium 80 on the body-facing side of the article highlights the slit area 90 while the internally visible serviceable indicium 80 in the front waist area highlights the target urination zone 95, the combination of which facilitates alignment of the article relative to the wearer's anus and gentiles during fitting.

Figure 15:
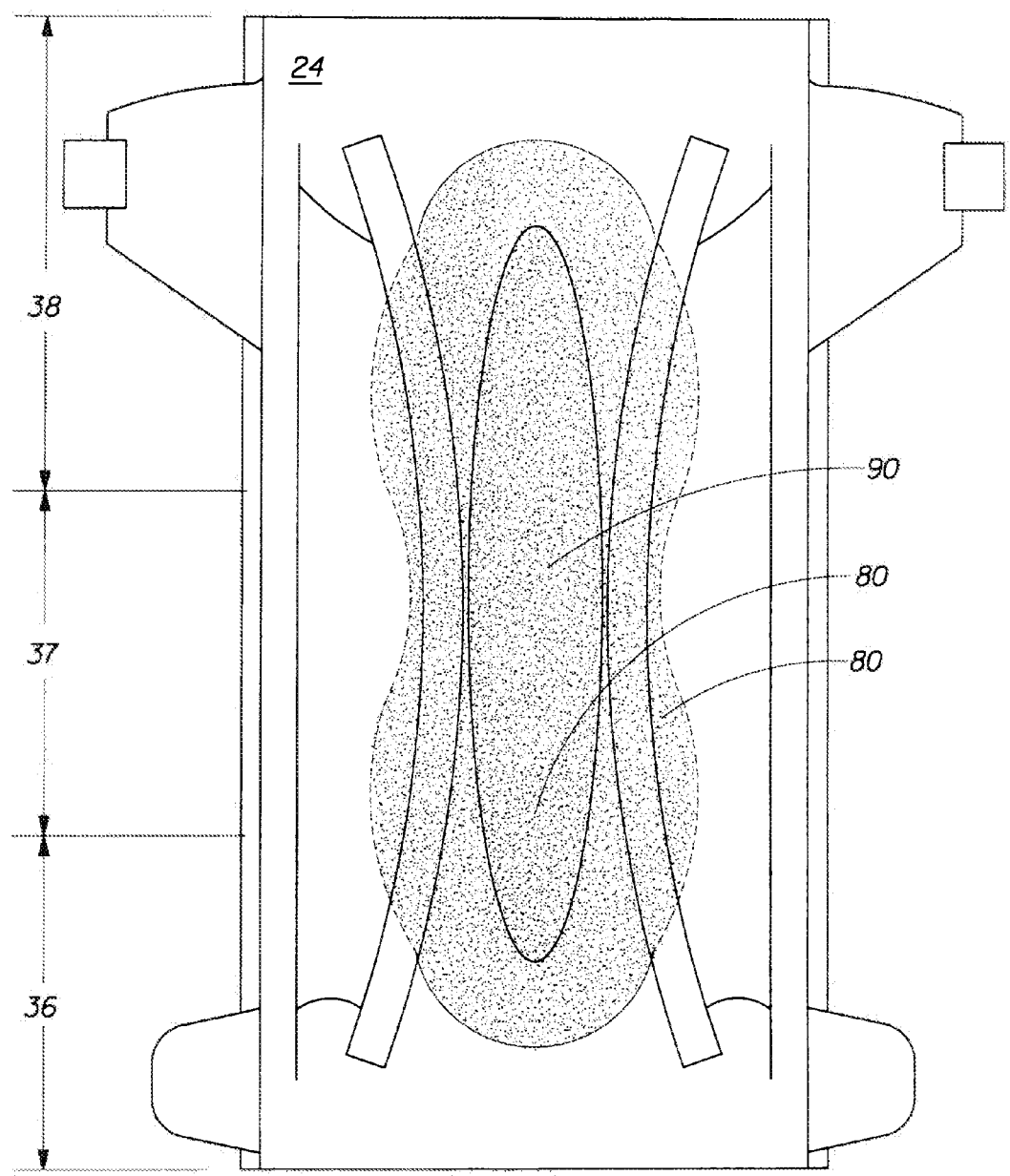
FIG. 15 is a plan view of the body-facing surface of the disposable absorbent article according to the present invention including an elastically foreshortened topsheet and a slit opening with visible serviceable indicia comprising two different patterns wherein the outer pattern aids in longitudinal positioning of the article and the inner pattern highlights the slit opening.
Figure 16:
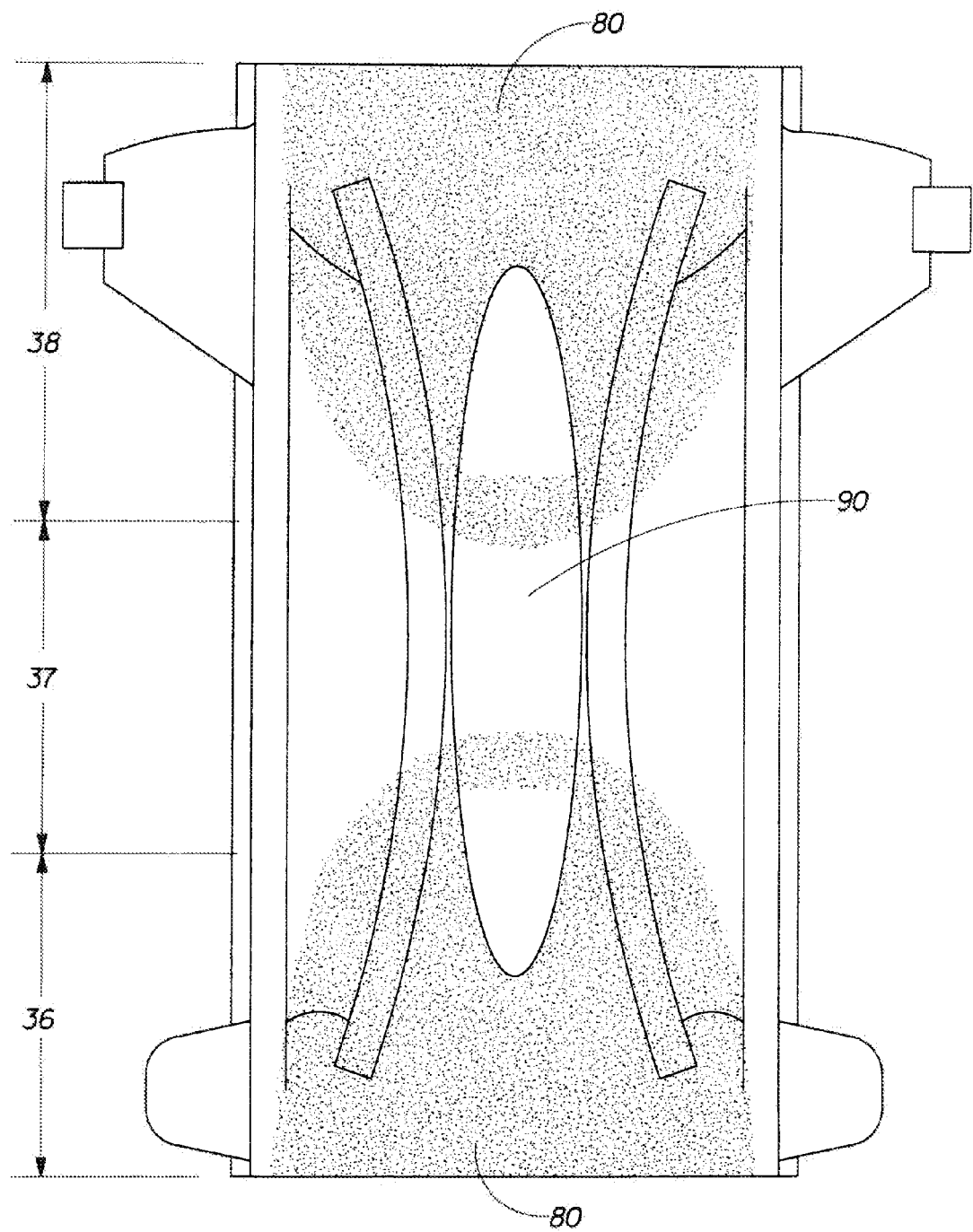
FIG. 16 is a plan view of the body-facing surface of the disposable absorbent article according to the present invention including an elastically foreshortened topsheet and a slit opening with visible serviceable indicia highlighting the first and second waist regions and the target zone for the anus relative to the slit opening.

The embodiment shown in FIG. 15 provides two different internally visible serviceable indicia 80, an outer indicium identifying the crotch region 37 and aiding in longitudinal positioning of the article and an inner indicium identifying the position of the slit or hole 90 in the elastically foreshortened top sheet 24 and aiding in positioning of the slit or hole 90 relative to the anus. In the embodiment shown in FIG. 16, the internally visible serviceable indicia 80 indicate the front and back waist areas and also highlight the target zone therebetween for the anus relative to the elasticated slit area.

Figure 17:
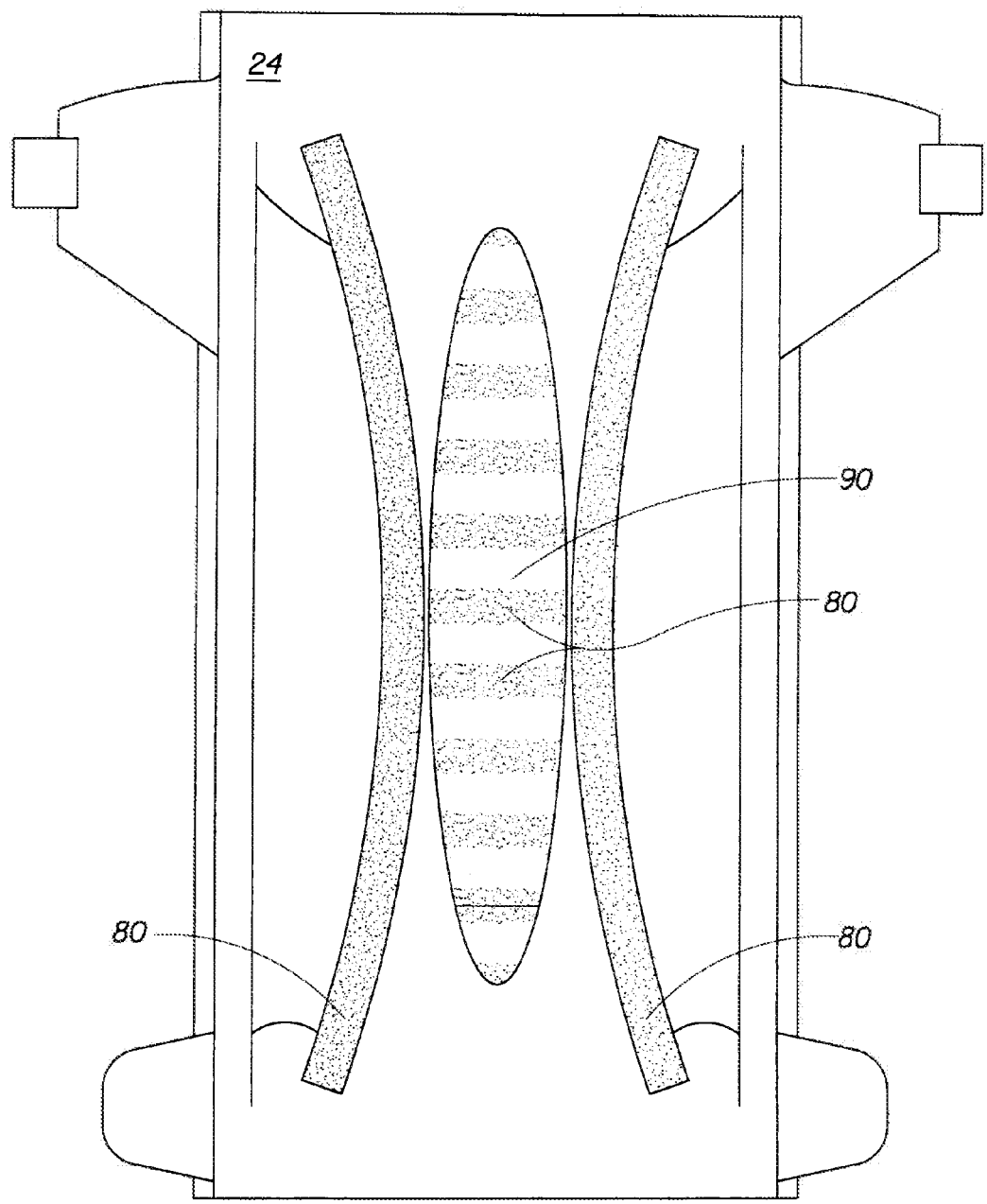
FIG. 17 is a plan view of the body-facing surface of the disposable absorbent article according to the present invention including an elastically foreshortened topsheet and a slit opening with visible serviceable indicia highlighting elasticity and positioning of the slit opening.

In the embodiment shown in FIG. 17, the internally visible serviceable indicia 80 on the body-facing side of an elastically foreshortened topsheet 24 comprise curved colored elastics to highlight the elasticity and the positioning of the hole 90 with respect to the anus. In addition, the stripe pattern underneath the topsheet 24 highlights the passage area for feces.

Figure 18:
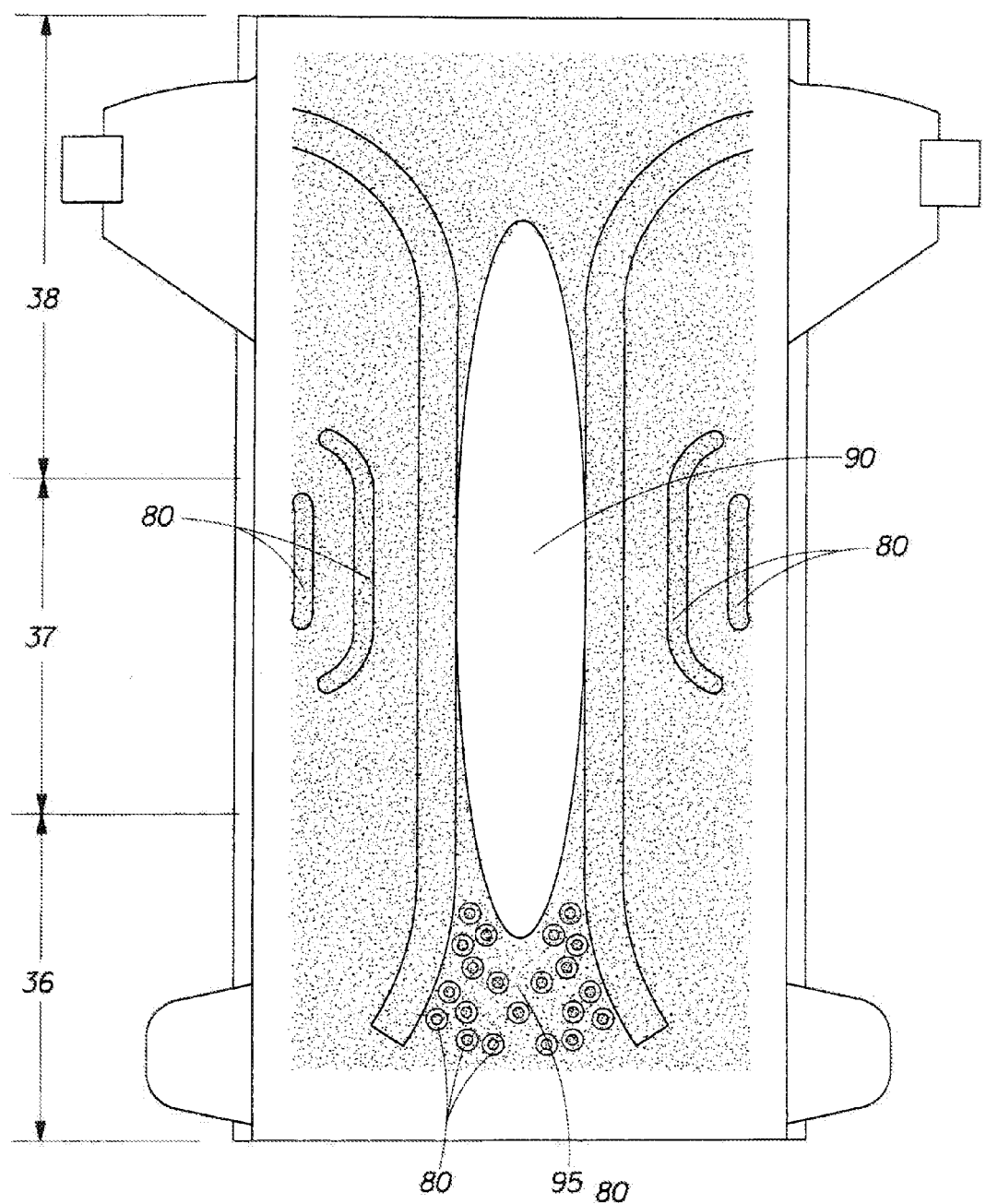
FIG. 18 is a plan view of the body-facing surface of the disposable absorbent article according to the present invention including an elastically foreshortened topsheet and a slit opening with visible serviceable indicia highlighting the crotch area, the slit opening and a target urination zone in the first waist region of the article.

FIG. 18 shows an alternative embodiment of a combination of different internally visible serviceable indicia 80 which highlight the crotch area to allow better longitudinal positioning of the diaper 20, indicate the target urination zone 95 in the front waist region, and highlight the slit or hole 90 disposed in the elastically foreshortened topsheet 24 providing alignment relative to the anus. The internally visible serviceable indicia 80 highlighting the slit or hole 90 can also provide masking of feces discharged by the wearer once it has passed through the hole 90.

In addition to the internally visible serviceable indicia 80, the diaper 20 may include a pair of barrier leg cuffs and a pair of elastically contractible gasketing leg cuffs. Each of the gasketing leg cuffs is disposed outside of a barrier leg cuff, adjacent to the longitudinal side edge. The barrier leg cuffs and the gasketing leg cuffs may be tinted a color complementing the pattern or color of the internally visible serviceable indicia 80 on the topsheet 24 providing an additional guide for aligning the article with the wearer's lower torso during fitting.

In addition, each of the gasketing leg cuffs may comprise one or more elastic strands covered by a portion of the longitudinal side edge of the backsheet 26 that is folded over the one or more elastic strands to form a finished gasketing leg cuff. For this embodiment, the garment-facing surface of the article may include serviceable indicia forming a pattern as previously described such that once the longitudinal side of the backsheet 26 is folded over the elastic strands forming the finished cuffs, the finished leg cuffs may include the serviceable indicia on the body-facing surface of the diaper 20.

Figure 19:
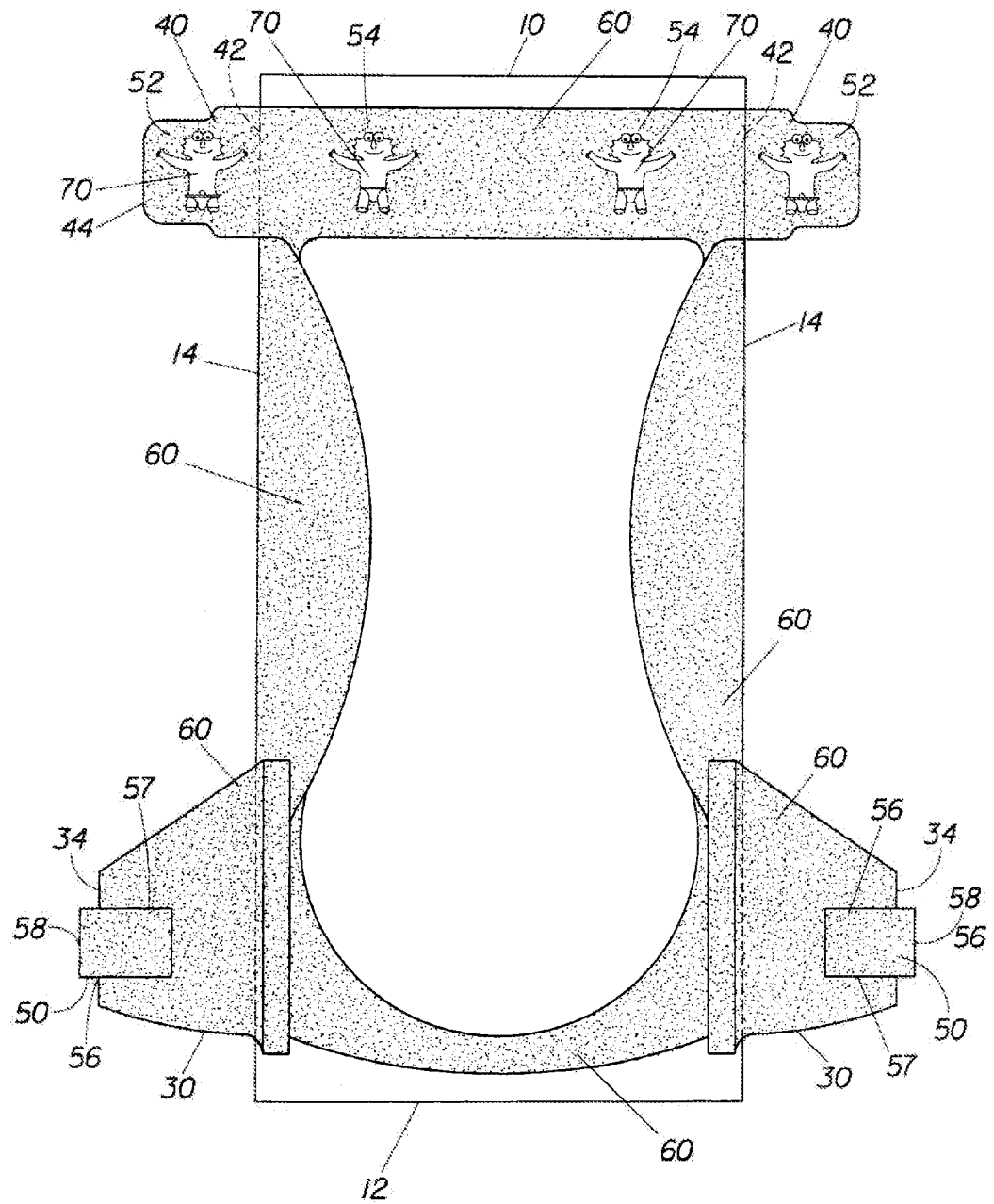
FIG. 19 is a plan view of a diaper including instructional serviceable indicia on the first and second landing members of the fastening system denoting a first fit and a second fit.

In addition to the features described above, the disposable absorbent article according to the present invention may include a fastening system 50 designed to facilitate an easy intuitive change. An example of an embodiment including such a fastening system 50 is shown in FIG. 19. For this embodiment, the fastening system 50 releasably attaches the first waist region 36 to the second waist region 38 and provides a first fit and a second fit. The first fit provides a loose fit enabling the article to be maneuvered about the wearer's lower torso during fitting and the second fit provides a secure fit about the wearer's waist. For instance, during the first fit, the diaper 20 may be fitted loosely around the wearer's ankles while standing and then pulled up around the wearer's waist and tightly secured by the second fit. The fastening system 50 includes primary and secondary landing members 52, 54 corresponding to the first fit and the second fit. In addition to the instructional serviceable indicia 70 previously described for providing guidance or instruction to the caregiver relative to the tightness of fit, the primary and secondary landing members 52, 54 can include instructional serviceable indicium 70 providing instruction to the caregiver corresponding to the first fit and the second fit.

For this embodiment, the fastening system 50 may include a hook and loop type fastener including at least one engaging component (male fastening component) and at least two landing zones (female fastening components). In this case, the two landing zones provide the primary and secondary landing members 52, 54. Alternatively, the fastener may include a tab and slot type fastener wherein the tab member includes a retaining element that interlocks with an opening such as a slit, slot, or loop as disclosed in commonly assigned U.S. Pat. No. 6,251,097 issued to Kline, et al. incorporated herein by reference. For this embodiment the tab and slot fastener comprises at least two slit, slot, or loop openings providing the primary and secondary landing members 52, 54. For tab and slot type fasteners, primary and secondary landing members 52, 54 are separated by a distance. For hook and loop type fasteners, the primary and secondary landing members 52, 54 may be separated by a distance or else contiguous.

The instructional serviceable indicia 70 disposed on the landing members include instructions designating matching connections between the tab members and first or second landing members 52, 54. The instructions might include graphics of characters illustrating the orientation and/or configuration of the diaper 20 during the first fit and the second fit. For instance, a graphic might illustrate a loose fitting diaper fitted about the waist of the character during the first fit and a tight fitting diaper secured about the waist of the character during the second fit.

Instructional serviceable indicia 70 disposed on the first and second landing members may be particularly useful where the diaper includes the versatility of being fitted to the wearer while the wearer is standing or lying down. For such an embodiment, the first fit may comprise fitting the diaper to the wearer while the wearer is standing in which case the diaper is fitted around the wearer's ankles by attaching the tabs to the first landing members and then pulled up around the lower torso of the wearer. Once the diaper is positioned around the lower torso, the diaper may be adjusted to achieve the second fit by removing the tabs from the first landing members and engaging them with the second landing members. For this embodiment, the graphic on the first landing member may include a character wearing a diaper around its ankles while the graphic on the second landing member includes a character wearing a diaper secured about its waist.

In addition to graphics, the instructional serviceable indicia 70 may also comprise words such as "ankles" and "waist" associated with the position of the article during the first fit and the second fit or they may designate the type of fit such as "loose" and "snug". Also, the instructional marks may comprise numbers such as one "1" and two "2" designating the first and second fits, respectively.

In the embodiment shown in FIG. 19, the fastening system 50 includes two tab members 56. Each tab member 56 has a tab proximal edge 57 disposed at the distal edge 34 of each of the first ear panels 30, a tab distal edge 58, a tab body-facing surface, and a tab garment-facing surface. Each tab member 56 includes fastening elements disposed proximate the tab distal edge 58. Second ear panels 40 are disposed along each longitudinal side edge 14 in the first waist region 36. Each second ear panel has a body-facing surface and a garment-facing surface, a proximal edge 42 joined to the longitudinal side edge 14 and a distal edge 44 opposite the proximal edge 42. A primary landing member 52 is disposed on the garment-facing surface of each of the second ear panels 40. The secondary landing member 54 is disposed on the garment-facing surface of the article in the first waist region 36. During fastening the primary landing member 52 provides a first fastening point wherein once the tab member 56 is engaged a first fit is achieved. The first fit provides a loose fit about the wearer enabling the diaper to be maneuvered about to achieve an effective orientation for wear. The second landing member 54 provides a second fastening point for achieving a second fit where the article is tightly secured about the waist of the wearer. For this embodiment the instructional serviceable indicia comprise graphics. The graphic on the first landing member 52 includes a character wearing a diaper around its ankles while the graphic on the second landing member 54 includes a character wearing a diaper secured about its waist.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable absorbent article having a first end region, a second end region and a crotch region between the first and second end regions, a longitudinal axis and a transverse axis that intersect in said crotch region of the absorbent article, said disposable absorbent article comprising:
   a liquid pervious topsheet, said liquid pervious topsheet having a body facing surface;
   a liquid impervious backsheet, said liquid impervious backsheet having a garment facing surface;
   a first a pair of side panels;
   a second pair of side panels that are spaced apart from said pair of side panels along said longitudinal axis;
   an absorbent core disposed between said topsheet and said backsheet; and
   a first internally visible serviceable indicium, said first internally visible serviceable indicium being at least partially located in said crotch region, said first internally visible serviceable indicium comprising an ink having a color, which distinguishes said first internally visible serviceable indicium from a region of said body facing surface of said liquid pervious topsheet, wherein said first internally visible serviceable indicium is visible on or through said body facing surface, wherein said first internally visible serviceable indicium comprises a pattern, and wherein said pattern comprises a variation of color along a length of said first internally visible serviceable indicium.

2. The disposable absorbent article of claim 1 wherein said first internally visible serviceable indicium comprises a concave portion.

3. The disposable absorbent article of claim 1 wherein said first internally visible serviceable indicium comprises a convex portion.

4. The disposable absorbent article of claim 1 wherein said first internally visible serviceable indicium is disposed on said liquid pervious topsheet.

5. The disposable absorbent article of claim 1 wherein said first internally visible serviceable indicium has a contour that is adapted to facilitate the placement or alignment of the absorbent article with an anatomic feature of a wearer chosen from at least one of a wearer's genitalia, and a wearer's buttocks.

6. The disposable absorbent article of claim 1 wherein said disposable absorbent article is an incontinence article.

7. The disposable absorbent article of claim 1 wherein said disposable absorbent article is a feminine protection article.

8. The disposable absorbent article of claim 1 wherein said first internally visible serviceable indicium is disposed substantially within said crotch region and at least minimally within at least one of said first end region and said second end region.

9. The disposable absorbent article of claim 1 wherein said pattern comprises a series of shapes and/or images.

10. The disposable absorbent article of claim 1 wherein said pattern comprises one or more dots, lines, stripes, regular shapes, irregular shapes, circles, swirls, ellipses, diamonds, squares, and combinations thereof.

11. A disposable absorbent article having a first end region, a second end region and a crotch region between the first and second end regions, a longitudinal axis and a transverse axis that intersect in said crotch region of the absorbent article, said disposable absorbent article comprising:
- a liquid pervious topsheet, said liquid pervious topsheet having a body facing surface;
- a liquid impervious backsheet, said liquid impervious backsheet having a garment facing surface;
- a first a pair of side panels;
- a second pair of side panels that are spaced apart from said first pair of side panels along said longitudinal axis of the article;
- wherein said first pair of side panels and said second pair of side panels extend laterally outward from said longitudinal axis substantially to the same extent;
- an absorbent core disposed between said topsheet and said backsheet; and
- a first internally visible serviceable indicium, said first internally visible serviceable indicium being at least partially located in said crotch region, said first internally visible serviceable indicium comprising an ink having a color, which distinguishes said first internally visible serviceable indicium from a region of said body facing surface of said liquid pervious topsheet, wherein said first internally visible serviceable indicium is visible on or through said body facing surface, wherein said first internally visible serviceable indicium comprises a pattern, and wherein said pattern comprises a variation of color along a length of said first internally visible serviceable indicium.

12. The disposable absorbent article of claim 11 wherein said first internally visible serviceable indicium comprises a concave portion.

13. The disposable absorbent article of claim 11 wherein said first internally visible serviceable indicium comprises a convex portion.

14. The disposable absorbent article of claim 11 wherein said first internally visible serviceable indicium is disposed on said liquid pervious topsheet.

15. The disposable absorbent article of claim 11 wherein said first internally visible serviceable indicium has a contour that is adapted to facilitate the placement or alignment of the absorbent article with an anatomic feature of a wearer chosen from at least one of a wearer's genitalia, and a wearer's buttocks.

16. The disposable absorbent article of claim 11 wherein said disposable absorbent article is an incontinence article.

17. The disposable absorbent article of claim 11 wherein said disposable absorbent article is a feminine protection article.

18. The disposable absorbent article of claim 11 wherein said first internally visible serviceable indicium is disposed substantially within said crotch region and at least minimally within at least one of said first end region and said second end region.

* * * * *